US012019066B2

(12) United States Patent
Piazza et al.

(10) Patent No.: US 12,019,066 B2
(45) Date of Patent: Jun. 25, 2024

(54) ASSAY WITH SYNAPTOBREVIN BASED MOIETY

(71) Applicant: BIOMADISON, INC., Del Mar, CA (US)

(72) Inventors: Timothy Piazza, McFarland, WI (US); Francis Mark Dunning, Madison, WI (US); Ward C Tucker, Monona, WI (US)

(73) Assignee: BioMadison, Inc., Del Mar, CA (US)

( * ) Notice: Subject to any disclaimer, the term of this patent is extended or adjusted under 35 U.S.C. 154(b) by 0 days.

(21) Appl. No.: 15/597,002

(22) Filed: May 16, 2017

(65) Prior Publication Data

US 2018/0074044 A1    Mar. 15, 2018

Related U.S. Application Data

(60) Provisional application No. 62/336,964, filed on May 16, 2016.

(51) Int. Cl.
| | | |
|---|---|---|
| *C07K 14/705* | (2006.01) | |
| *C07K 14/435* | (2006.01) | |
| *C12Q 1/37* | (2006.01) | |
| *G01N 33/50* | (2006.01) | |
| *G06T 7/00* | (2017.01) | |

(52) U.S. Cl.
CPC .................. *G01N 33/5005* (2013.01); *C07K 14/43595* (2013.01); *C07K 14/705* (2013.01); *C12Q 1/37* (2013.01); *G06T 7/001* (2013.01); *G06T 7/0016* (2013.01); *C07K 2319/50* (2013.01); *C07K 2319/60* (2013.01); *C07K 2319/70* (2013.01); *G01N 2333/33* (2013.01); *G01N 2333/952* (2013.01); *G06T 2207/30072* (2013.01); *G06T 2207/30242* (2013.01)

(58) Field of Classification Search
None
See application file for complete search history.

(56) References Cited

U.S. PATENT DOCUMENTS

| | | | | |
|---|---|---|---|---|
| 6,100,234 A * | 8/2000 | Huber | ............... | A61K 31/69 |
| | | | | 514/3.8 |
| 8,969,016 B2 * | 3/2015 | Fish | ............... | C12Q 1/37 |
| | | | | 435/7.21 |
| 9,249,449 B2 * | 2/2016 | Miyawaki | ............... | C12Q 1/37 |
| 9,274,121 B2 * | 3/2016 | Atapattu | ............... | G01N 33/582 |
| 9,303,285 B2 * | 4/2016 | Piazza | ............... | G01N 33/582 |
| 9,453,254 B2 * | 9/2016 | Tucker | ............... | C12Q 1/37 |
| 9,624,529 B2 | 4/2017 | Oyler | | |
| 2002/0110834 A1 * | 8/2002 | Benkovic | ............... | C12Q 1/37 |
| | | | | 435/7.1 |
| 2002/0132327 A1 * | 9/2002 | Hay | ............... | C07K 14/4705 |
| | | | | 435/195 |
| 2003/0059847 A1 * | 3/2003 | Backes | ............... | C07K 1/047 |
| | | | | 506/15 |
| 2003/0092629 A1 * | 5/2003 | Tang | ............... | C07K 5/0207 |
| | | | | 514/17.8 |
| 2003/0100707 A1 * | 5/2003 | Hwang | ............... | C07K 19/00 |
| | | | | 530/350 |
| 2004/0038375 A1 * | 2/2004 | Pedersen | ............... | C07K 14/811 |
| | | | | 435/252.3 |
| 2004/0137597 A1 * | 7/2004 | Davydov | ............... | C07K 14/00 |
| | | | | 435/226 |
| 2004/0146938 A1 * | 7/2004 | Nguyen | ............... | C12N 9/6467 |
| | | | | 435/7.1 |
| 2005/0074889 A1 * | 4/2005 | Chumakov | ............... | C12Q 1/6897 |
| | | | | 435/456 |
| 2006/0024289 A1 * | 2/2006 | Ruggles | ............... | C12N 9/6424 |
| | | | | 424/94.64 |
| 2006/0105953 A1 | 5/2006 | Lacoste et al. | | |
| 2006/0134722 A1 | 6/2006 | Chapman et al. | | |
| 2008/0032917 A1 * | 2/2008 | Li | ............... | C12Q 1/18 |
| | | | | 530/324 |
| 2008/0064054 A1 * | 3/2008 | Fernandez-Salas | ............... | |
| | | | | G01N 33/542 |
| | | | | 435/29 |

(Continued)

FOREIGN PATENT DOCUMENTS

| | | |
|---|---|---|
| WO | 2006010106 | 1/2006 |
| WO | 2009035476 | 3/2009 |

(Continued)

OTHER PUBLICATIONS

Neefjes et al., Fluorescent probes for proteolysis: tools for drug discovery; Nature Reviews, Drug Discovery, vol. 3, pp. 58-68 2004 (Year: 2004).*
Sequence Alignment of SEQ ID No. 11 with AXS40811. Dec. 24, 2009 (first entry). 2 pages. (Year: 2009).*
Sequence Alignment of SEQ ID No. 12 with AAB41899. Feb. 8, 2001 (first entry). 2 pages. (Year: 2001).*
Sequence Alignment of SEQ ID No. 13 with AEQ21129. May 3, 2007 (first entry). 2 pages. (Year: 2007).*
Sequence Alignment of SEQ ID No. 14 with AYL83675. Jan. 6, 2011 (first entry). 3 pages. (Year: 2011).*
Sequence Alignment of SEQ ID No. 15 with BAN378839. Jun. 6, 2013 (first entry). 2 pages. (Year: 2013).*

(Continued)

*Primary Examiner* — Lora E Barnhart Driscoll
*Assistant Examiner* — Catherine Konopka
(74) *Attorney, Agent, or Firm* — Fish IP Law, LLP

(57) ABSTRACT

Compositions and methods for improved cell-based methods of characterizing botulinum neurotoxins are provided. Cells utilized in these methods include a reporting construct that is cleaved following uptake and processing of botulinum neurotoxin by the cell, resulting in proteolysis of the portion of the reporting construct that is released following cleavage. The released portion includes a fluorophore and amino acid substitutions or sequences that enhance the rate of proteolysis. A pair of reporting constructs can be utilized in which one member of the pair is modified to resist cleavage by the botulinum neurotoxin while co-localizing with the remaining member of the pair.

9 Claims, 28 Drawing Sheets
Specification includes a Sequence Listing.

(56) References Cited

U.S. PATENT DOCUMENTS

| | | | |
|---|---|---|---|
| 2009/0263836 A1* | 10/2009 | Fernandez-Salas | ............................ G01N 33/5014 435/7.32 |
| 2010/0034777 A1 | 2/2010 | Wandless et al. | |
| 2010/0086930 A1* | 4/2010 | Soukka | ................ G01N 33/542 435/6.16 |
| 2011/0033866 A1* | 2/2011 | Fish | ................ C12Q 1/37 435/7.1 |
| 2011/0165191 A1* | 7/2011 | Ranga | ................ A61K 31/7088 424/208.1 |
| 2011/0269141 A1* | 11/2011 | Murayama | ................ A61K 31/7088 435/6.13 |
| 2012/0309039 A1* | 12/2012 | Atapattu | ................ G01N 33/582 435/23 |
| 2012/0322092 A1* | 12/2012 | Tucker | ................ C12Q 1/37 435/23 |
| 2014/0024063 A1* | 1/2014 | Piazza | ................ G01N 33/582 435/23 |
| 2014/0249295 A1 | 9/2014 | Bonger et al. | |
| 2014/0255361 A1 | 9/2014 | Wandless et al. | |
| 2014/0323391 A1* | 10/2014 | Tsalik | ................ C12Q 1/689 514/2.7 |
| 2015/0010931 A1 | 1/2015 | Oyler et al. | |
| 2015/0118701 A1* | 4/2015 | Tucker | ................ C07K 14/43595 435/23 |
| 2015/0159193 A1* | 6/2015 | Tucker | ................ G01N 21/6408 435/23 |
| 2015/0315574 A1* | 11/2015 | Wilusz | ................ A61K 48/00 424/489 |
| 2015/0329896 A1* | 11/2015 | Oyler | ................ C12Q 1/37 435/7.4 |
| 2016/0025626 A1 | 1/2016 | Dos Santos Fegadolli et al. | |
| 2016/0069862 A1* | 3/2016 | Tucker | ................ C12Q 1/37 435/23 |
| 2016/0151466 A1* | 6/2016 | Dunning | ................ C07K 14/705 424/172.1 |
| 2017/0097350 A1* | 4/2017 | Tucker | ................ G01N 21/6408 |
| 2018/0072780 A1* | 3/2018 | Atapattu | ................ G01N 33/582 |
| 2018/0074044 A1* | 3/2018 | Piazza | ................ G01N 33/5005 |

FOREIGN PATENT DOCUMENTS

| | | | |
|---|---|---|---|
| WO | 2010127400 | 11/2010 | |
| WO | WO-2011047265 A1 * | 4/2011 | ............... C12Q 1/37 |
| WO | 2021047325 | 3/2021 | |

OTHER PUBLICATIONS

Sequence Alignment of SEQ ID No. 16 with BDN17243. Mar. 9, 2017 (first entry). 2 pages. (Year: 2017).*

Sequence Alignment of SEQ ID No. 17 with AAM04299. Oct. 9, 2001 (first entry). 2 pages. (Year: 2011).*

Sequence Alignment of SEQ ID No. 18 with ABG73429. May 1, 2003 (first entry). 2 pages. (Year: 2003).*

Sequence Alignment of SEQ ID No. 19 with BCR43598. Jul. 28, 2016 (first entry). 2 pages. (Year: 2016).*

Kota et al., 'A high content imaging assay for identification of Botulinum neurotoxin inhibitors', Journal of Visualized Experiments, vol. 93, Article No. 51915, pp. 1-10 (Nov. 2014).

Basavanna et al., 'Development of a cell-based functional assay for the detection of Clostridium botulinum neurotoxin types A and E', International Journal of Microbiology, vol. 2013, Article ID. 593219, pp. 1-7 (2013).

Dong et al., 'Using fluorescent sensors to detect botulinum neurotoxin activity in vitro and in living cells', PNAS, vol. 101, No. 41, pp. 14701-14706 (Oct. 12, 2004).

International Search Report International application No. PCT/US2017/032954 International filing date May 16, 2017.

John R. Houser et al., An Improved Short-lived Fluorescent Protein Transcriptional Reporter for *Saccharomyces cerevisiae*; Yeast, 2012; 29: 519-530.

Thomas M. Kitzler, Complement Modulates the function of the Ubiquitin—Proteasome System and Endoplasmic Reticulum-Associated Degradation in Glomerular Epithelial Cells; Biochimica et Biophysica Acta 1823 (2012) 1007-1016.

Alexandra Reis et al., The CRY box: a second APCcdh1-dependent Degron in Mammalian cdc20; EMBO reports vol. 7, No. 10, 2006, 1040-1045.

European Search Report dated Dec. 16, 2019 for EP Application No. 17800032.9 in the name of BioMadison, Inc. (16 pages).

* cited by examiner

```
  1         10        20        30        40        50        60        70
115        124       134       144       154       164       174        18
ATGGTGAGCAAGGGCGAGGAGCTGTTCACCGGGGTGGTGCCCATCCTGGTCGAGCTGGACGGCGACGTAA
                                                                    YFP 150       160       170       180       190       200        21
          264       274       284       294       304       314        32
CATCTGCACCACCGGCAAGCTGCCCGTGCCCTGGCCCACCCTCGTGACCACCTTCGGCTACGGCCTGCAG
                                                                    YFP 290       300       310       320       330       340        35
          404       414       424       434       444       454        46
TCCAGGAGCGCACCATCTTCTTCAAGGACGACGGCAACTACAAGACCCGCGCCGAGGTGAAGTTCGAGGG
                                                                    YFP 430       440       450       460       470       480        49
          544       554       564       574       584       594        60
AAGCTGGAGTACAACTACAACAGCCACAACGTCTATATCATGGCCGACAAGCAGAAGAACGGCATCAAGG
                                                                    YFP 570       580       590       600       610       620        63
          684       694       704       714       724       734        74
CCCCATCGGCGACGGCCCCGTGCTGCTGCCCGACAACCACTACCTGAGCTACCAGTCCGCCCTGAGCAAA
                                                                    YFP 710       720       730       740       750       760        77
          824       834       844       854       864       874        88
TGGACGAGCTGTACAAGAGTGGAGGCATGTCGGCTACCGCTGCCACCGTCCCGCCTGCCGCCCCGGCCGG
              YFP       Linker                     VAMP2

850       860       870       880       890       900        91
          964       974       984       994      1,004     1,014       1,0
GTGGATGAGGTGGTGGACATCATGAGGGTGAATGTGGACAAGGTCCTGGAGCGRGACCAGAAGCTATCGG
                                                  VAMP2

990      1,000     1,010     1,020     1,030     1,040       1,0
         1,104     1,114     1,124     1,134     1,144     1,154       1,1
GCGCAAATACTGGTGGAAAAACCTCAAGATGATGATCATCTTGGGAGTGATTTGCGCCATCATCCTCATC
                                                  VAMP2
```

Plasmid pMD0032ORF encoding YFP-synaptobrevin (VAMP2) SEQ ID NO. 1
(continued on FIG. 6A-B)

*FIG. 6A-A*

```
   0         80        90        100       110       120       130       140
   |         |         |         |         |         |         |         |
  84        194       204       214       224       234       244       254
AACGGCCACAAGTTCAGCGTGTCCGGCGAGGGCGAGGGCGATGCCACCTACGGCAAGCTGACCCTGAAGTT
            YFP
  10        220       230       240       250       260       270       280
   |         |         |         |         |         |         |         |
  24        334       344       354       364       374       384       394
GTGCTTCGCCCGCTACCCCGACCACATGAAGCAGCACGACTTCTTCAAGTCCGCCATGCCCGAAGGCTACG
            YFP
  50        360       370       380       390       400       410       420
   |         |         |         |         |         |         |         |
  64        474       484       494       504       514       524       534
GCGACACCCTGGTGAACCGCATCGAGCTGAAGGGCATCGACTTCAAGGAGGACGGCAACATCCTGGGGCAC
            YFP
  90        500       510       520       530       540       550       560
   |         |         |         |         |         |         |         |
  04        614       624       634       644       654       664       674
GTGAACTTCAAGATCCGCCACAACATCGAGGACGGCAGCGTGCAGCTCGCCGACCACTACCAGCAGAACAC
            YFP
  30        640       650       660       670       680       690       700
   |         |         |         |         |         |         |         |
  44        754       764       774       784       794       804       814
AGACCCCAACGAGAAGCGCGATCACATGGTCCTGCTGGAGTTCGTGACCGCCGCCGGGATCACTCTCGGCA
            YFP
  70        780       790       800       810       820       830       840
   |         |         |         |         |         |         |         |
  84        894       904       914       924       934       944       954
GCGAGGGTGGCCCCCCTGCACCTCCTCCAAATCTTACCAGTAACAGGAGACTGCAGCAGACCCAGGCCCAG
            VAMP2
  10        920       930       940       950       960       970       980
   |         |         |         |         |         |         |         |
 024      1,034     1,044     1,054     1,064     1,074     1,084     1,094
GAACTGGATGATCGCGCAGATGCCCTCCAGGCAGGGGCCTCCCAGTTTGAAACAAGTGCAGCCAAGCTCAA
            VAMP2
 050      1,060     1,070     1,077
  |         |         |         |
  64      1,174     1,184     1,191
CATCATCATCGTTTACTTCAGCACTTAA
```

Plasmid pMD0032ORF encoding YFP-synaptobrevin (VAMP2) SEQ ID NO. 1
(continued from FIG. 6A-A)

*FIG. 6A-B*

```
  1         10        20        30        40        50        60        70
118        127       137       147       157       167       177       18
ATGGTGAGCAAGGGCGAGGAGCTGTTCACCGGGGTGGTGCCCATCCTGGTCGAGCTGGACGGCGACGTAA
└─────────────────────────────── ECFP ───────────────────────────────

150       160       170       180       190       200       21
           267       277       287       297       307       317       32
CATCTGCACCACCGGCAAGCTGCCCGTGCCCCTGGCCCACCCTCGTGACCACCCTGACCTGGGGCGTGCAG
└─────────────────────────────── ECFP ───────────────────────────────

290       300       310       320       330       340       35
           407       417       427       437       447       457       46
TCCAGGAGCGCACCATCTTCTTCAAGGACGACGGCAACTACAAGACCCGCGCCGAGGTGAAGTTCGAGGG
└─────────────────────────────── ECFP ───────────────────────────────

430       440       450       460       470       480       49
           547       557       567       577       587       597       60
AAGCTGGAGTACAACTACATCAGCCACAACGTCTATATCACCGCCGACAAGCAGAAGAACGGCATCAAGG
└─────────────────────────────── ECFP ───────────────────────────────

570       580       590       600       610       620       63
           687       697       707       717       727       737       74
CCCCATCGGCGACGGCCCCGTGCTGCTGCCCGACAACCACTACCTGAGCACCCAGTCCGCCCTGAGCAAA
└─────────────────────────────── ECFP ───────────────────────────────

710       720       730       740       750       760       77
           827       837       847       857       867       877       88
TGGACGAGCTGTACAAGAGTGGAGGCATGTCGGCTACCGCTGCCACCGTCCCGCCTGCCGCCCCGGCCGG
└───── ECFP ─────┘└─ Linker ─┘└─────────────── VAMP2 ───────────────

850       860       870       880       890       900       91
           967       977       987       997      1,007     1,017      1,0
GTGGATGAGGTGGTGGACATCATGAGGGTGAATGTGGACAAGGTCCTGGAGCGRGACCAGAAGCTATCGG
└─────────────────────────────── VAMP2 ──────────────────────────────

990      1,000     1,010     1,020     1,030     1,040      1,0
          1,107     1,117     1,127     1,137     1,147     1,157      1,1
GCGCAAATACTGGTGGAAAAACCTCAAGATGATGATCATCTTGGGAGTGATTTGCGCCATCATCCTCATC
└─────────────────────────────── VAMP2 ──────────────────────────────
```

Plasmid pMD0034ORF encoding CFP-synaptobrevin (VAMP2) SEQ ID NO. 2 (continued on FIG. 6B-B)

*FIG. 6B-A*

```
  0         80         90        100        110        120        130        140
  7        197        207        217        227        237        247        257
ACGGCCACAAGTTCAGCGTGTCCGGCGAGGGCGAGGGCGATGCCACCTACGGCAAGCTGACCCTGAAGTT
           ECFP 0        220        230        240        250        260        270        280
  7        337        347        357        367        377        387        397
TGCTTCAGCCGCTACCCCGACCACATGAAGCAGCACGACTTCTTCAAGTCCGCCATGCCCGAAGGCTACG
           ECFP 0        360        370        380        390        400        410        420
  7        477        487        497        507        517        527        537
CGACACCCTGGTGAACCGCATCGAGCTGAAGGGCATCGACTTCAAGGAGGACGGCAACATCCTGGGGCAC
           ECFP 0        500        510        520        530        540        550        560
  7        617        627        637        647        657        667        677
CCAACTTCAAGATCCGCCACAACATCGAGGACGGCAGCGTGCAGCTCGCCGACCACTACCAGCAGAACAC
           ECFP 0        640        650        660        670        680        690        700
  7        757        767        777        787        797        807        817
GACCCCAACGAGAAGCGCGATCACATGGTCCTGCTGGAGTTCGTGACCGCCGCCGGGATCACTCTCGGCA
           ECFP 0        780        790        800        810        820        830        840
  7        897        907        917        927        937        947        957
CGAGGGTGGCCCCCCTGCACCTCCTCCAAATCTTACCAGTAACAGGAGACTGCAGCAGACCCAGGCCCAG
                                        VAMP2

0        920        930        940        950        960        970        980
 27       1,037      1,047      1,057      1,067      1,077      1,087      1,097
AACTGGATGATCGCGCAGATGCCCTCCAGGCAGGGGCCTCCCAGTTTGAAACAAGTGCAGCCAAGCTCAA
           VAMP2

50       1,060      1,070      1,077
 67       1,177      1,187      1,194
ATCATCATCGTTTACTTCAGCACTTAA
           VAMP2
```

Plasmid pMD0034ORF encoding CFP-synaptobrevin (VAMP2) SEQ ID NO. 2 (continued from FIG. 6B-A)

*FIG. 6B-B*

```
  1         10        20        30        40        50        60        70
124        133       143       153       163       173       183       19
ATGGTGAGCAAGGGCGAGGAGCTGTTCACCGGGGTGGTGCCCATCCTGGTCGAGCTGGACGGCGACGTAA
                                                                    YFP 150       160       170       180       190       200       21
           273       283       293       303       313       323       33
CATCTGCACCACCGGCAAGCTGCCCGTGCCCCTGGCCCACCCTCGTGACCACCTTCGGCTACGGCCTGCAG
                                                                     YFP 290       300       310       320       330       340       35
           413       423       433       443       453       463       47
TCCAGGAGCGCACCATCTTCTTCAAGGACGACGGCAACTACAAGACCCGCGCCGAGGTGAAGTTCGAGGG
                                                                    YFP 430       440       450       460       470       480       49
           553       563       573       583       593       603       61
AAGCTGGAGTACAACTACAACAGCCACAACGTCTATATCATGGCCGACAAGCAGAAGAACGGCATCAAGG
                                                                    YFP 570       580       590       600       610       620       63
           693       703       713       723       733       743       75
CCCCATCGGCGACGGCCCCGTGCTGCTGCCCGACAACCACTACCTGAGCTACCAGTCCGCCCTGAGCAAA
                                                                    YFP 710       720       730       740       750       760       77
           833       843       853       863       873       883       89
TGGACGAGCTGTACAAGAGTGGAGGCATGTCGGCTACCGCTGCCACCGTCCCGCCTGCCGCCCCGGCCGG
       YFP          Linker                         VAMP2

850       860       870       880       890       900       91
           973       983       993      1,003     1,013     1,023     1,03
GTGGATGAGGTGGTGGACATCATGAGGGTGAATGTGGACAAGGTCCTGGAGCGRGACCAGAAGCTATCGG
                                                  VAMP2

990      1,000     1,010     1,020     1,030     1,040     1,05
          1,113     1,123     1,133     1,143     1,153     1,163     1,1
GCGCAAATACTGGTGGAAAAACCTCAAGATGATGATCATCTTGGGAGTGATTTGCGCCATCATCCTCATC
                                                  VAMP2
```

Plasmid pMD0034ORF encoding YFP-synaptobrevin (VAMP2) SEQ ID NO. 3
(continued on FIG. 6C-B)

*FIG. 6C-A*

```
  0        80        90       100       110       120       130       140
  |         |         |         |         |         |         |         |
 93       203       213       223       233       243       253       263
  |         |         |         |         |         |         |         |
AACGGCCACAAGTTCAGCGTGTCCGGCGAGGGCGAGGGCGATGCCACCTACGGCAAGCTGACCCTGAAGTT
              YFP                                                       >

10       220       230       240       250       260       270       280
  |         |         |         |         |         |         |         |
 33       343       353       363       373       383       393       403
  |         |         |         |         |         |         |         |
GTGCTTCGCCCGCTACCCCGACCACATGAAGCAGCACGACTTCTTCAAGTCCGCCATGCCCGAAGGCTACG
              YFP                                                       >

50       360       370       380       390       400       410       420
  |         |         |         |         |         |         |         |
 73       483       493       503       513       523       533       543
  |         |         |         |         |         |         |         |
GCGACACCCTGGTGAACCGCATCGAGCTGAAGGGCATCGACTTCAAGGAGGACGGCAACATCCTGGGGCAC
              YFP                                                       >

90       500       510       520       530       540       550       560
  |         |         |         |         |         |         |         |
 13       623       633       643       653       663       673       683
  |         |         |         |         |         |         |         |
GTGAACTTCAAGATCCGCCACAACATCGAGGACGGCAGCGTGCAGCTCGCCGACCACTACCAGCAGAACAC
              YFP                                                       >

30       640       650       660       670       680       690       700
  |         |         |         |         |         |         |         |
 53       763       773       783       793       803       813       823
  |         |         |         |         |         |         |         |
AGACCCCAACGAGAAGCGCGATCACATGGTCCTGCTGGAGTTCGTGACCGCCGCCGGGATCACTCTCGGCA
              YFP                                                       >

70       780       790       800       810       820       830       840
  |         |         |         |         |         |         |         |
 93       903       913       923       933       943       953       963
  |         |         |         |         |         |         |         |
GCGAGGGTGGCCCCCCTGCACCTCCTCCAAATCTTACCAGTAACAGGAGACTGCAGCAGACCCAGGCCCAG
              VAMP2                                                     >

10       920       930       940       950       960       970       980
  |         |         |         |         |         |         |         |
033      1,043     1,053     1,063     1,073     1,083     1,093     1,103
  |         |         |         |         |         |         |         |
GAACTGGATGATCGCGCAGATGCCCTCCAGGCAGGGGCCTCCCAGTTTGAAACAAGTGCAGCCAAGCTCAA
              VAMP2                                                     >

50      1,060     1,070    1,077
  |         |         |        |
 73      1,183     1,193    1,200
  |         |         |        |
CATCATCATCGTTTACTTCAGCACTTAA
              VAMP2        >
```

Plasmid pMD0034ORF encoding YFP-synaptobrevin (VAMP2) SEQ ID NO. 3
(continued from FIG. 6C-A)

*FIG. 6C-B*

```
  1         10        20        30        40        50        60        70
ATGGTGAGCAAGGGCGAGGAGCTGTTCACCGGGGTGGTGCCCATCCTGGTCGAGCTGGACGGCGACGTAA
                                        ECFP 150       160       170       180       190       200        21
CATCTGCACCACCGGCAAGCTGCCCGTGCCCTGGCCCACCCTCGTGACCACCCTGACCTGGGGCGTGCAG
                                        ECFP 290       300       310       320       330       340        35
TCCAGGAGCGCACCATCTTCTTCAAGGACGACGGCAACTACAAGACCCGCGCCGAGGTGAAGTTCGAGGG
                                        ECFP 430       440       450       460       470       480        49
AAGCTGGAGTACAACTACATCAGCCACAACGTCTATATCACCGCCGACAAGCAGAAGAACGGCATCAAGG
                                        ECFP 570       580       590       600       610       620        63
CCCCATCGGCGACGGCCCCGTGCTGCTGCCCGACAACCACTACCTGAGCACCCAGTCCGCCCTGAGCAAA
                                        ECFP 710       720       730       740       750       760        77
TGGACGAGCTGTACAAGAGTGGAGGCATGTCGGCTACCGCTGCCACCGTCCCGCCTGCCGCCCCGGCCGG
     ECFP       Linker                        VAMP2

850       860       870       880       890       900        91
GTGGATGAGGTGGTGGACATCATGAGGGTGAATGTGGACAAGGTCCTGGAGCGRGACCAGAAGCTATCGG
                                        VAMP2

990      1,000     1,010     1,020     1,030     1,040       1,0
GCGCAAATACTGGTGGAAAAACCTCAAGATGATGATCATCTTGGGAGTGATTTGCGCCATCATCCTCATC
                                        VAMP2
```

Plasmid pMD0071ORF encoding CFP-synaptobrevin (VAMP2) SEQ ID NO. 4 (continued on FIG. 6D-B)

*FIG. 6D-A*

```
    0        80         90        100        110        120        130        140
    |         |         |          |          |          |          |          |
AACGGCCACAAGTTCAGCGTGTCCGGCGAGGGCGAGGGCGATGCCACCTACGGCAAGCTGACCCTGAAGTT
         ECFP
```

```
   10        220        230        240        250        260        270        280
    |         |          |          |          |          |          |          |
GTGCTTCAGCCGCTACCCCGACCACATGAAGCAGCACGACTTCTTCAAGTCCGCCATGCCCGAAGGCTACG
         ECFP
```

```
   50        360        370        380        390        400        410        420
    |         |          |          |          |          |          |          |
GCGACACCCTGGTGAACCGCATCGAGCTGAAGGGCATCGACTTCAAGGAGGACGGCAACATCCTGGGGCAC
         ECFP
```

```
   90        500        510        520        530        540        550        560
    |         |          |          |          |          |          |          |
GCCAACTTCAAGATCCGCCACAACATCGAGGACGGCAGCGTGCAGCTCGCCGACCACTACCAGCAGAACAC
         ECFP
```

```
   30        640        650        660        670        680        690        700
    |         |          |          |          |          |          |          |
AGACCCCAACGAGAAGCGCGATCACATGGTCCTGCTGGAGTTCGTGACCGCCGCCGGGATCACTCTCGGCA
         ECFP
```

```
   70        780        790        800        810        820        830        840
    |         |          |          |          |          |          |          |
GCGAGGGTGGCCCCCCTGCACCTCCTCCAAATCTTACCAGTAACAGGAGACTGCAGCAGACCCAGGCCCAG
         VAMP2
```

```
   10        920        930        940        950        960        970        980
    |         |          |          |          |          |          |          |
GAACTGGATGATCGCGCAGATGCCCTCCAGGCAGGGGCCTCCGTGTTTGAAACAAGTGCAGCCAAGCTCAA
         VAMP2
```

```
  050       1,060      1,070      1,077
    |         |          |          |
CATCATCATCGTTTACTTCAGCACTTAA
         VAMP2
```

Plasmid pMD0071ORF encoding CFP-synaptobrevin (VAMP2) SEQ ID NO. 4
(continued from FIG. 6D-A)

*FIG. 6D-B*

```
  1         10        20        30        40        50        60        70
124        133       143       153       163       173       183       19
ATGGTGAGCAAGGGCGAGGAGCTGTTCACCGGGGTGGTGCCCATCCTGGTCGAGCTGGACGGCGACGTAA
|                                    YFP                                |

150       160       170       180       190       200       21
           273       283       293       303       313       323       33
CATCTGCACCACCGGCAAGCTGCCCGTGCCCTGGCCCACCCTCGTGACCACCTTCGGCTACGGCCTGCAG
|                                    YFP                                |

290       300       310       320       330       340       35
           413       423       433       443       453       463       47
TCCAGGAGCGCACCATCTTCTTCAAGGACGACGGCAACTACAAGACCCGCGCCGAGGTGAAGTTCGAGGG
|                                    YFP                                |

430       440       450       460       470       480       49
           553       563       573       583       593       603       61
AAGCTGGAGTACAACTACAACAGCCACAACGTCTATATCATGGCCGACAAGCAGAAGAACGGCATCAAGG
|                                    YFP                                |

570       580       590       600       610       620       63
           693       703       713       723       733       743       75
CCCCATCGGCGACGGCCCCGTGCTGCTGCCCGACAACCACTACCTGAGCTACCAGTCCGCCCTGAGCAAA
|                                    YFP                                |

710       720       730       740       750       760       77
           833       843       853       863       873       883       89
TGGACGAGCTGTACAAGAGTGGAGGCATGTCGGCTACCGCTGCCACCGTCCCGCCTGCCGCCCCGGCCGG
|     YFP        |  Linker  |                 VAMP2                     |

850       860       870       880       890       900       91
           973       983       993      1,003     1,013     1,023      1,0
GTGGATGAGGTGGTGGACATCATGAGGGTGAATGTGGACAAGGTCCTGGAGCGGACCAGAAGCTATCGG
|                                   VAMP2                                |

990      1,000     1,010     1,020     1,030     1,040      1,0
          1,113     1,123     1,133     1,143     1,153     1,163      1,1
GCGCAAATACTGGTGGAAAAACCTCAAGATGATGATCATCTTGGGAGTGATTTGCGCCATCATCCTCATC
|                                   VAMP2                                |
```

Plasmid pMD0071ORF encoding YFP-synaptobrevin (VAMP2) SEQ ID NO. 5
(continued on FIG. 6E-B)

*FIG. 6E-A*

```
 0            80           90          100          110          120          130          140
 |            |            |            |            |            |            |            |
 93          203          213          223          233          243          253          263
AACGGCCACAAGTTCAGCGTGTCCGGCGAGGGCGAGGGCGATGCCACCTACGGCAAGCTGACCCTGAAGTT
              YFP 10          220          230          240          250          260          270          280
 |            |            |            |            |            |            |            |
 33          343          353          363          373          383          393          403
GTGCTTCGCCCGCTACCCCGACCACATGAAGCAGCACGACTTCTTCAAGTCCGCCATGCCCGAAGGCTACG
              YFP 50          360          370          380          390          400          410          420
 |            |            |            |            |            |            |            |
 73          483          493          503          513          523          533          543
GCGACACCCTGGTGAACCGCATCGAGCTGAAGGGCATCGACTTCAAGGAGGACGGCAACATCCTGGGGCAC
              YFP 90          500          510          520          530          540          550          560
 |            |            |            |            |            |            |            |
 13          623          633          643          653          663          673          683
GTGAACTTCAAGATCCGCCACAACATCGAGGACGGCAGCGTGCAGCTCGCCGACCACTACCAGCAGAACAC
              YFP 30          640          650          660          670          680          690          700
 |            |            |            |            |            |            |            |
 53          763          773          783          793          803          813          823
AGACCCCAACGAGAAGCGCGATCACATGGTCCTGCTGGAGTTCGTGACCGCCGCCGGGATCACTCTCGGCA
              YFP 70          780          790          800          810          820          830          840
 |            |            |            |            |            |            |            |
 93          903          913          923          933          943          953          963
GCGAGGGTGGCCCCCCTGCACCTCCTCCAAATCTTACCAGTAACAGGAGACTGCAGCAGACCCAGGCCCAG
              VAMP2

10          920          930          940          950          960          970          980
 |            |            |            |            |            |            |            |
033         1,043        1,053        1,063        1,073        1,083        1,093        1,103
GAACTGGATGATCGCGCAGATGCCCTCCAGGCAGGGGCCTCCCAGTTTGAAACAAGTGCAGCCAAGCTCAA
              VAMP2

050        1,060        1,070        1,077
 |           |            |            |
 73         1,183        1,193        1,200
CATCATCATCGTTTACTTCAGCACTTAA
              VAMP2
```

Plasmid pMD0071ORF encoding YFP-synaptobrevin (VAMP2) SEQ ID NO. 5
(continued from FIG. 6E-A)

```
  1         10        20        30        40        50        60        70
133        142       152       162       172       182       192        20
ATGGTGAGCAAGGGCGAGGAGCTGTTCACCGGGGTGGTGCCCATCCTGGTCGAGCTGGACGGCGACGTAA
                                                                    YFP 150       160       170       180       190       200        21
            282       292       302       312       322       332        34
CATCTGCACCACCGGCAAGCTGCCCGTGCCCTGGCCCACCCTCGTGACCACCTTCGGCTACGGCCTGCAG
                                                                    YFP 290       300       310       320       330       340        35
            422       432       442       452       462       472        48
TCCAGGAGCGCACCATCTTCTTCAAGGACGACGGCAACTACAAGACCCGCGCCGAGGTGAAGTTCGAGGG
                                                                    YFP 430       440       450       460       470       480        49
            562       572       582       592       602       612        62
AAGCTGGAGTACAACTACAACAGCCACAACGTCTATATCATGGCCGACAAGCAGAAGAACGGCATCAAGG
                                                                    YFP 570       580       590       600       610       620        63
            702       712       722       732       742       752        76
CCCCATCGGCGACGGCCCCGTGCTGCTGCCCGACAACCACTACCTGAGCTACCAGTCCGCCCTGAGCAAA
                                                                    YFP 710       720       730       740       750       760        77
            842       852       862       872       882       892        90
TGGACGAGCTGTACAAGTCTGGAGGCAAGCTTGCAATGGTGAGCAAGGGCGAGGAGCTGTTCACCGGGGT
       YFP              Linker                          YFP 850       860       870       880       890       900        91
            982       992      1,002     1,012     1,022     1,032      1,04
GGCGATGCCACCTACGGCAAGCTGACCCTGAAGTTCATCTGCACCACCGGCAAGCTGCCCGTGCCCTGGC
                                                                    YFP 990      1,000     1,010     1,020     1,030     1,040       1,0
           1,122     1,132     1,142     1,152     1,162     1,172       1,1
CGACTTCTTCAAGTCCGCCATGCCCGAAGGCTACGTCCAGGAGCGCACCATCTTCTTCAAGGACGACGGC
                                                                    YFP 1,130     1,140     1,150     1,160     1,170     1,180       1,1
           1,262     1,272     1,282     1,292     1,302     1,312       1,3
TCGACTTCAAGGAGGACGGCAACATCCTGGGGCACAAGCTGGAGTACAACTACAACAGCCACAACGTCTA
                                                                    YFP
``` pMD0183ORF encoding YFP-YFP-synaptobrevin (VAMP2) SEQ ID NO. 8 (continued on FIG. 6F-B)

FIG. 6F-B

```
         80        90       100       110       120       130       140
        212       222       232       242       252       262       272
ACGGCCACAAGTTCAGCGTGTCCGGCGAGGGCGAGGGCGATGCCACCTACGGCAAGCTGACCCTGAAGTT
                                      YFP 220       230       240       250       260       270       280
        352       362       372       382       392       402       412
TGCTTCGCCCGCTACCCCGACCACATGAAGCAGCACGACTTCTTCAAGTCCGCCATGCCCGAAGGCTACG
                                      YFP 360       370       380       390       400       410       420
        492       502       512       522       532       542       552
CGACACCCTGGTGAACCGCATCGAGCTGAAGGGCATCGACTTCAAGGAGGACGGCAACATCCTGGGGCAC
                                      YFP 500       510       520       530       540       550       560
        632       642       652       662       672       682       692
TGAACTTCAAGATCCGCCACAACATCGAGGACGGCAGCGTGCAGCTCGCCGACCACTACCAGCAGAACAC
                                      YFP 640       650       660       670       680       690       700
        772       782       792       802       812       822       832
GACCCCAACGAGAAGCGCGATCACATGGTCCTGCTGGAGTTCGTGACCGCCGCCGGGATCACTCTCGGCA
                                      YFP 780       790       800       810       820       830       840
        912       922       932       942       952       962       972
GGTGCCCATCCTGGTCGAGCTGGACGGCGACGTAAACGGCCACAAGTTCAGCGTGTCCGGCGAGGGCGAG
                                      YFP 920       930       940       950       960       970       980
       1,052     1,062     1,072     1,082     1,092     1,102     1,112
CCACCCTCGTGACCACCTTCGGCTACGGCCTGCAGTGCTTCGCCCGCTACCCCGACCACATGAAGCAGCA
                                      YFP 50  1,060     1,070     1,080     1,090     1,100     1,110     1,120
   82  1,192     1,202     1,212     1,222     1,232     1,242     1,252
AACTACAAGACCCGCGCCGAGGTGAAGTTCGAGGGCGACACCCTGGTGAACCGCATCGAGCTGAAGGGCA
                                      YFP 90  1,200     1,210     1,220     1,230     1,240     1,250     1,260
   22  1,332     1,342     1,352     1,362     1,372     1,382     1,392
TATCATGGCCGACAAGCAGAAGAACGGCATCAAGGTGAACTTCAAGATCCGCCACAACATCGAGGACGGC
                                      YFP
``` pMD0183ORF encoding YFP-YFP-synaptobrevin (VAMP2) SEQ ID NO. 8
(continued from 6F-A and continued on FIG. 6F-C)

```
     1,270      1,280      1,290      1,300      1,310      1,320      1,3
     1,402      1,412      1,422      1,432      1,442      1,452      1,4
AGCGTGCAGCTCGCCGACCACTACCAGCAGAACACCCCCATCGGCGACGGCCCCGTGCTGCTGCCCGACA
                                  YFP 1,410      1,420      1,430      1,440      1,450      1,460      1,4
     1,542      1,552      1,562      1,572      1,582      1,460      1,4
GGAGTTCGTGACCGCCGCCGGGATCACTCTCGGCATGGACGAGCTGTACAAGAGTGGAGGCATGTCGGCT
                      YFP                              Linker      VAMP2

1,550      1,560      1,570      1,580      1,590      1,600      1,6
     1,550      1,560      1,570      1,580      1,590      1,600      1,6
CCAGTAACAGGAGACTGCAGCAGACCCAGGCCCAGGTGGATGAGGTGGTGGACATCATGAGGGTGAATGT
                              VAMP2

1,690      1,700      1,710      1,720      1,730      1,740      1,7
     1,690      1,700      1,710      1,720      1,730      1,740      1,7
GCCTCCCAGTTTGAAACAAGTGCAGCCAAGCTCAAGCGCAAATACTGGTGGAAAAACCTCAAGATGATGA
                              VAMP2
``` pMD0183ORF encoding YFP-YFP-synaptobrevin (VAMP2) SEQ ID NO. 8
(continued from 6F-B and continued on FIG. 6F-D)

*FIG. 6F-C*

```
30      1,340      1,350      1,360      1,370      1,380      1,390      1,400
62      1,472      1,482      1,492      1,502      1,512      1,522      1,532
ACCACTACCTGAGCTACCAGTCCGCCCTGAGCAAAGACCCCAACGAGAAGCGCGATCACATGGTCCTGCT
                                        YFP 70      1,480      1,490      1,500      1,510      1,520      1,530      1,540
70      1,480      1,490      1,500      1,510      1,520      1,530      1,540
ACCGCTGCCACCGTCCCGCCTGCCGCCCCGGCCGGCGAGGGTGGCCCCCCTGCACCTCCTCCAAATCTTA
                                        VAMP2

10      1,620      1,630      1,640      1,650      1,660      1,670      1,680
10      1,620      1,630      1,640      1,650      1,660      1,670      1,680
GGACAAGGTCCTGGAGCGRGACCAGAAGCTATCGGAACTGGATGATCGCGCAGATGCCCTCCAGGCAGGG
                                        VAMP2

50      1,760      1,770      1,780      1,790      1,800      1,812
50      1,760      1,770      1,780      1,790      1,800      1,812
TCATCTTGGGAGTGATTTGCGCCATCATCCTCATCATCATCGTTTACTTCAGCACTTAA
                                        VAMP2
``` pMD0183ORF encoding YFP-YFP-synaptobrevin (VAMP2) SEQ ID NO. 8
(continued from FIG. 6F-C)

*FIG. 6F-D*

```
  1         10        20        30        40        50        60        70
  ATGGTGAGCAAGGGCGAGGAGCTGTTCACCGGGGTGGTGCCCATCCTGGTCGAGCTGGACGGCGACGTAA
  |_____
                                      ECFP 150       160       170       180       190       200       21
  CATCTGCACCACCGGCAAGCTGCCCGTGCCCTGGCCCACCCTCGTGACCACCCTGACCTGGGGCGTGCAG
  |_____
                                      ECFP 290       300       310       320       330       340       35
  TCCAGGAGCGCACCATCTTCTTCAAGGACGACGGCAACTACAAGACCCGCGCCGAGGTGAAGTTCGAGGG
  |_____
                                      ECFP                               EC 430       440       450       460       470       480       49
  AAGCTGGAGTACAACTACATCAGCCACAACGTCTATATCACCGCCGACAAGCAGAAGAACGGCATCAAGG
  |_____
                                      ECFP 570       580       590       600       610       620       63
  CCCCATCGGCGACGGCCCCGTGCTGCTGCCCGACAACCACTACCTGAGCACCCAGTCCGCCCTGAGCAAA
  |_____
                                      ECFP 710       720       730       740       750       760       77
  TGGACGAGCTGTACAAGAGTGGAGGCATGTCGGCTACCGCTGCCACCGTCCCGCCTGCCGCCCCGGCCGG
  |_____ECFP_____| |__Linker__| |_____VAMP2_____

850       860       870       880       890       900       91
  GTGGATGAGGTGGTGGACATCATGAGGGTGAATGTGGACAAGGTCCTGGAGCGRGACCAGAAGCTATCGG
  |_____
                                      VAMP2

990       1,000     1,010     1,020     1,030     1,040     1,0
  GCGCAAATACTGGTGGAAAAACCTCAAGATGATGATCATCTTGGGAGTGATTTGCGCCATCATCCTCATC
  |_____
                                      VAMP2
```

Plasmid pMD0185ORF encoding CFP-synaptobrevin (VAMP2) SEQ ID NO. 6 (continued on FIG. 6G-B)

*FIG. 6G-A*

```
  0           80        90       100       110       120       130       140
ACGGCCACAAGTTCAGCGTGTCCGGCGAGGGCGAGGGCGATGCCACCTACGGCAAGCTGACCCTGAAGTT
               ECFP 0          220       230       240       250       260       270       280
TGCTTCAGCCGCTACCCCGACCACATGAAGCAGCACGACTTCTTCAAGTCCGCCATGCCCGAAGGCTACG
               ECFP 0          360       370       380       390       400       410       420
CGACACCCTGGTGAACCGCATCGAGCTGAAGGGCATCGACTTCAAGGAGGACGGCAACATCCTGGGGCAC
               ECFP 0          500       510       520       530       540       550       560
CCAACTTCAAGATCCGCCACAACATCGAGGACGGCAGCGTGCAGCTCGCCGACCACTACCAGCAGAACAC
               ECFP 0          640       650       660       670       680       690       700
GACCCCAACGAGAAGCGCGATCACATGGTCCTGCTGGAGTTCGTGACCGCCGCCGGGATCACTCTCGGCA
               ECFP 0          780       790       800       810       820       830       840
CGAGGGTGGCCCCCCTGCACCTCCTCCAAATCTTACCAGTAACAGGAGACTGCAGCAGACCCAGGCCCAG
               VAMP2

0          920       930       940       950       960       970       980
AACTGAATAATCGCGCAAATGCCCTCCAGGCAGGGGCCTCCGTGTTTGAAACAAGTGCAGCCAAGCTCAA
               VAMP2

50        1,060     1,070     1,077
ATCATCATCGTTTACTTCAGCACTTAA
               VAMP2
```

Plasmid pMD0185ORF encoding CFP-synaptobrevin (VAMP2) SEQ ID NO. 6
(continued from FIG. 6G-A)

*FIG. 6G-B*

```
  1         10        20        30        40        50        60      7
367        376       386       396       406       416       426     43
ATGAAGCAGCACGACTTCTTCAAGTCCGCCATGCCCGAAGGCTACGTCCAGGAGCGCACCATCTTCTTCA
                                   YFP 150       160       170       180       190       200      21
         516       526       536       546       556       566      57
GCTGAAGGGCATCGACTTCAAGGAGGACGGCAACATCCTGGGGCACAAGCTGGAGTACAACTACAACAGC
                                   YFP 290       300       310       320       330       340      35
         656       666       676       686       696       706      71
TCGAGGACGGCAGCGTGCAGCTCGCCGACCACTACCAGCAGAACACCCCCATCGGCGACGGCCCCGTGCT
                                   YFP 430       440       450       460       470       480      49
         796       806       816       826       836       846      85
ATGGTCCTGCTGGAGTTCGTGACCGCCGCCGGGATCACTCTCGGCATGGACGAGCTGTACAAGAGTGGAG
                                   YFP                              Linker 570       580       590       600       610       620      63
         936       946       956       966       976       986      99
TCCAAATCTTACCAGTAACAGGAGACTGCAGCAGACCCAGGCCCAGGTGGATGAGGTGGTGGACATCATG
                                  VAMP2

710       720       730       740       750       760      77
        1,076     1,086     1,096     1,106     1,116     1,126    1,13
TCCAGGCAGGGGCCTCCCAGTTTGAAACAAGTGCAGCCAAGCTCAAGCGCAAATACTGGTGGAAAAACCT
                                  VAMP2

843
1,209
TAA
    VAMP2
```

Plasmid pMD0185ORF encoding YFP-synaptobrevin (VAMP2) SEQ ID NO. 7
(continued on FIG.6H-B)

*FIG. 6H-A*

```
    0          80         90        100        110        120        130        140
    |          |          |          |          |          |          |          |
   36         446        456        466        476        486        496        506
AAGGACGACGGCAACTACAAGACCCGCGCCGAGGTGAAGTTCGAGGGCGACACCCTGGTGAACCGCATCGA
                                            YFP 10         220        230        240        250        260        270        280
    |          |          |          |          |          |          |          |
   76         586        596        606        616        626        636        646
CCACAACGTCTATATCATGGCCGACAAGCAGAAGAACGGCATCAAGGTGAACTTCAAGATCCGCCACAACA
                                            YFP 50         360        370        380        390        400        410        420
    |          |          |          |          |          |          |          |
   16         726        736        746        756        766        776        786
TGCTGCCCGACAACCACTACCTGAGCTACCAGTCCGCCCTGAGCAAAGACCCCAACGAGAAGCGCGATCAC
                                            YFP 90         500        510        520        530        540        550        560
    |          |          |          |          |          |          |          |
   56         866        876        886        896        906        916        926
GGCATGTCGGCTACCGCTGCCACCGTCCCGCCTGCCGCCCCGGCCGGCGAGGGTGGCCCCCCTGCACCTCC
                                           VAMP2

30         640        650        660        670        680        690        700
    |          |          |          |          |          |          |          |
   96       1,006      1,016      1,026      1,036      1,046      1,056      1,066
GAGGGTGAATGTGGACAAGGTCCTGGAGCGRGACCAGAAGCTATCGGAACTGGATGATCGCGCAGATGCCC
                                           VAMP2

70         780        790        800        810        820        830        840
    |          |          |          |          |          |          |          |
   36       1,146      1,156      1,166      1,176      1,186      1,196      1,206
TCAAGATGATGATCATCTTGGGAGTGATTTGCGCCATCATCCTCATCATCATCGTTTACTTCAGCACT
                                           VAMP2
```

Plasmid pMD0185ORF encoding YFP-synaptobrevin (VAMP2)  SEQ ID NO. 7
(continued from FIG. 6H-A)

SEQUENCE LISTING

<160> NUMBER OF SEQ ID NOS: 23

<210> SEQ ID NO 1
<211> LENGTH: 1077
<212> TYPE: DNA
<213> ORGANISM: Artificial Sequence
<220> FEATURE:
<223> OTHER INFORMATION: pMD0032 YFPVAMP2, plasmid encoding for YFPVAMP2
      construct

<400> SEQUENCE: 1

| | | | | | |
|---|---|---|---|---|---|
| atggtgagca | agggcgagga | gctgttcacc | ggggtggtgc | ccatcctggt | cgagctggac | 60 |
| ggcgacgtaa | acggccacaa | gttcagcgtg | tccggcgagg | gcgagggcga | tgccacctac | 120 |
| ggcaagctga | ccctgaagtt | catctgcacc | accggcaagc | tgcccgtgcc | ctggcccacc | 180 |
| ctcgtgacca | ccttcggcta | cggcctgcag | tgcttcgccc | gctaccccga | ccacatgaag | 240 |
| cagcacgact | tcttcaagtc | cgccatgccc | gaaggctacg | tccaggagcg | caccatcttc | 300 |
| ttcaaggacg | acggcaacta | caagacccgc | gccgaggtga | agttcgaggg | cgacaccctg | 360 |
| gtgaaccgca | tcgagctgaa | gggcatcgac | ttcaaggagg | acggcaacat | cctggggcac | 420 |
| aagctggagt | acaactacaa | cagccacaac | gtctatatca | tggccgacaa | gcagaagaac | 480 |
| ggcatcaagg | tgaacttcaa | gatccgccac | aacatcgagg | acggcagcgt | gcagctcgcc | 540 |
| gaccactacc | agcagaacac | ccccatcggc | gacggccccg | tgctgctgcc | cgacaaccac | 600 |
| tacctgagct | accagtccgc | cctgagcaaa | gaccccaacg | agaagcgcga | tcacatggtc | 660 |
| ctgctggagt | tcgtgaccgc | cgccgggatc | actctcggca | tggacgagct | gtacaagagt | 720 |
| ggaggcatgt | cggctaccgc | tgccaccgtc | ccgcctgccg | cccggcgg | cgagggtggc | 780 |
| cccctgcac | ctcctccaaa | tcttaccagt | aacaggagac | tgcagcagac | ccaggccag | 840 |
| gtggatgagg | tggtggacat | catgagggtg | aatgtggaca | aggtcctgga | gcgrgaccag | 900 |
| aagctatcgg | aactggatga | tcgcgcagat | gccctccagg | caggggcctc | ccagtttgaa | 960 |
| acaagtgcag | ccaagctcaa | gcgcaaatac | tggtggaaaa | acctcaagat | gatgatcatc | 1020 |
| ttgggagtga | tttgcgccat | catcctcatc | atcatcatcg | tttacttcag | cacttaa | 1077 |

<210> SEQ ID NO 2
<211> LENGTH: 1077
<212> TYPE: DNA
<213> ORGANISM: Artificial Sequence
<220> FEATURE:
<223> OTHER INFORMATION: pMD0034 ECFPVAMP, plasmid encoding for
      ECFPVAMP2 construct

<400> SEQUENCE: 2

| | | | | | |
|---|---|---|---|---|---|
| atggtgagca | agggcgagga | gctgttcacc | ggggtggtgc | ccatcctggt | cgagctggac | 60 |
| ggcgacgtaa | acggccacaa | gttcagcgtg | tccggcgagg | gcgagggcga | tgccacctac | 120 |
| ggcaagctga | ccctgaagtt | catctgcacc | accggcaagc | tgcccgtgcc | ctggcccacc | 180 |
| ctcgtgacca | ccctgacctg | gggcgtgcag | tgcttcagcc | gctaccccga | ccacatgaag | 240 |
| cagcacgact | tcttcaagtc | cgccatgccc | gaaggctacg | tccaggagcg | caccatcttc | 300 |
| ttcaaggacg | acggcaacta | caagacccgc | gccgaggtga | agttcgaggg | cgacaccctg | 360 |
| gtgaaccgca | tcgagctgaa | gggcatcgac | ttcaaggagg | acggcaacat | cctggggcac | 420 |
| aagctggagt | acaactacat | cagccacaac | gtctatatca | ccgccgacaa | gcagaagaac | 480 |
| ggcatcaagg | ccaacttcaa | gatccgccac | aacatcgagg | acggcagcgt | gcagctcgcc | 540 |
| gaccactacc | agcagaacac | ccccatcggc | gacggccccg | tgctgctgcc | cgacaaccac | 600 |

```
tacctgagca cccagtccgc cctgagcaaa gaccccaacg agaagcgcga tcacatggtc    660
ctgctggagt tcgtgaccgc cgccgggatc actctcggca tggacgagct gtacaagagt    720
ggaggcatgt cggctaccgc tgccaccgtc ccgcctgccg cccggccgg cgagggtggc    780 cccctgcac ctcctccaaa tcttaccagt aacaggagac tgcagcagac ccaggcccag    840
gtggatgagg tggtggacat catgagggtg aatgtggaca aggtcctgga gcgrgaccag    900
aagctatcgg aactggatga tcgcgcagat gccctccagg caggggcctc ccagtttgaa    960
acaagtgcag ccaagctcaa gcgcaaatac tggtggaaaa acctcaagat gatgatcatc   1020
ttgggagtga tttgcgccat catcctcatc atcatcatcg tttacttcag cacttaa      1077
```

<210> SEQ ID NO 3
<211> LENGTH: 1076
<212> TYPE: DNA
<213> ORGANISM: Artificial Sequence
<220> FEATURE:
<223> OTHER INFORMATION: pMD0034 YFPVAMP2, plasmid encoding for YFPVAMP2 construct

<400> SEQUENCE: 3

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccttcggcta cggcctgcag tgcttcgccc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagct accagtccgc cctgagcaaa gaccccaacg agaagcgcga tcacatggtc    660
ctgctggagt tcgtgaccgc cgccgggatc actctcggca tggacgagct gtacaagagt    720
ggaggcatgt cggctaccgc tgccaccgtc ccgcctgccg cccggccgg cgagggtggc    780 cccctgcacc tcctccaaat cttaccagta acaggagact gcagcagacc caggcccagg    840
tggatgaggt ggtggacatc atgagggtga atgtggacaa ggtcctggag cgrgaccaga    900
agctatcgga actggatgat cgcgcagatg ccctccaggc aggggcctcc cagtttgaaa    960
caagtgcagc caagctcaag cgcaaatact ggtggaaaaa cctcaagatg atgatcatct   1020
tgggagtgat ttgcgccatc atcctcatca tcatcatcgt ttacttcagc acttaa       1076
```

<210> SEQ ID NO 4
<211> LENGTH: 1077
<212> TYPE: DNA
<213> ORGANISM: Artificial Sequence
<220> FEATURE:
<223> OTHER INFORMATION: pMD0071 ECFPVAMP2, plasmid encoding for ECFPVAMP2 construct

<400> SEQUENCE: 4

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
```

| | |
|---|---|
| ggcaagctga cccctgaagtt catctgcacc accggcaagc tgcccgtgcc ctggcccacc | 180 |
| ctcgtgacca ccctgacctg gggcgtgcag tgcttcagcc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacat cagccacaac gtctatatca ccgccgacaa gcagaagaac | 480 |
| ggcatcaagg ccaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actctcggca tggacgagct gtacaagagt | 720 |
| ggaggcatgt cggctaccgc tgccaccgtc ccgcctgccg ccccggccgg cgagggtggc | 780 |
| cccccctgcac ctcctccaaa tcttaccagt aacaggagac tgcagcagac ccaggcccag | 840 |
| gtggatgagg tggtggacat catgagggtg aatgtgaca aggtcctgga gcgrgaccag | 900 |
| aagctatcgg aactggatga tcgcgcagat gccctccagg caggggcctc cgtgtttgaa | 960 |
| acaagtgcag ccaagctcaa gcgcaaatac tggtggaaaa acctcaagat gatgatcatc | 1020 |
| ttgggagtga tttgcgccat catcctcatc atcatcatcg tttacttcag cacttaa | 1077 |

<210> SEQ ID NO 5
<211> LENGTH: 1077
<212> TYPE: DNA
<213> ORGANISM: Artificial Sequence
<220> FEATURE:
<223> OTHER INFORMATION: pMD0071 YFPVAMP2, plasmid encoding for YFPVAMP2 construct

<400> SEQUENCE: 5

| | |
|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga cccctgaagtt catctgcacc accggcaagc tgcccgtgcc ctggcccacc | 180 |
| ctcgtgacca ccttcggcta cggcctgcag tgcttcgccc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagct accagtccgc cctgagcaaa gaccccaacg agaagcgcga tcacatggtc | 660 |
| ctgctggagt tcgtgaccgc cgccgggatc actctcggca tggacgagct gtacaagagt | 720 |
| ggaggcatgt cggctaccgc tgccaccgtc ccgcctgccg ccccggccgg cgagggtggc | 780 |
| cccccctgcac ctcctccaaa tcttaccagt aacaggagac tgcagcagac ccaggcccag | 840 |
| gtggatgagg tggtggacat catgagggtg aatgtgaca aggtcctgga gcgrgaccag | 900 |
| aagctatcgg aactggatga tcgcgcagat gccctccagg caggggcctc ccagtttgaa | 960 |
| acaagtgcag ccaagctcaa gcgcaaatac tggtggaaaa acctcaagat gatgatcatc | 1020 |
| ttgggagtga tttgcgccat catcctcatc atcatcatcg tttacttcag cacttaa | 1077 |

<210> SEQ ID NO 6
<211> LENGTH: 1077
<212> TYPE: DNA
<213> ORGANISM: Artificial Sequence
<220> FEATURE:
<223> OTHER INFORMATION: pMD0185 ECFPVAMP2, plasmid encoding for ECFPVAMP2 construct

<400> SEQUENCE: 6

| | | | | | |
|---|---|---|---|---|---|
| atggtgagca | agggcgagga | gctgttcacc | ggggtggtgc | ccatcctggt | cgagctggac | 60 |
| ggcgacgtaa | acggccacaa | gttcagcgtg | tccggcgagg | gcgagggcga | tgccacctac | 120 |
| ggcaagctga | ccctgaagtt | catctgcacc | accggcaagc | tgcccgtgcc | ctggcccacc | 180 |
| ctcgtgacca | ccctgacctg | gggcgtgcag | tgcttcagcc | gctaccccga | ccacatgaag | 240 |
| cagcacgact | tcttcaagtc | cgccatgccc | gaaggctacg | tccaggagcg | caccatcttc | 300 |
| ttcaaggacg | acggcaacta | caagacccgc | gccgaggtga | agttcgaggg | cgacaccctg | 360 |
| gtgaaccgca | tcgagctgaa | gggcatcgac | ttcaaggagg | acggcaacat | cctggggcac | 420 |
| aagctggagt | acaactacat | cagccacaac | gtctatatca | ccgccgacaa | gcagaagaac | 480 |
| ggcatcaagg | ccaacttcaa | gatccgccac | aacatcgagg | acggcagcgt | gcagctcgcc | 540 |
| gaccactacc | agcagaacac | ccccatcggc | gacggccccg | tgctgctgcc | cgacaaccac | 600 |
| tacctgagca | cccagtccgc | cctgagcaaa | gaccccaacg | agaagcgcga | tcacatggtc | 660 |
| ctgctggagt | tcgtgaccgc | cgccgggatc | actctcggca | tggacgagct | gtacaagagt | 720 |
| ggaggcatgt | cggctaccgc | tgccaccgtc | ccgcctgccg | ccccggccgg | cgagggtggc | 780 |
| cccctgcac | ctcctccaaa | tcttaccagt | aacaggagac | tgcagcagac | ccaggcccag | 840 |
| gtggatgagg | tggtggacat | catgagggtg | aatgtggaca | aggtcctgga | gcgrgaccag | 900 |
| aagctatcgg | aactgaataa | tcgcgcaaat | gccctccagg | caggggcctc | cgtgtttgaa | 960 |
| acaagtgcag | ccaagctcaa | gcgcaaatac | tggtggaaaa | acctcaagat | gatgatcatc | 1020 |
| ttgggagtga | tttgcgccat | catcctcatc | atcatcatcg | tttacttcag | cacttaa | 1077 |

<210> SEQ ID NO 7
<211> LENGTH: 843
<212> TYPE: DNA
<213> ORGANISM: Artificial Sequence
<220> FEATURE:
<223> OTHER INFORMATION: pMD0185 YFPVAMP2, plasmid encoding for YFPVAMP2 construct

<400> SEQUENCE: 7

| | | | | | |
|---|---|---|---|---|---|
| atgaagcagc | acgacttctt | caagtccgcc | atgcccgaag | gctacgtcca | ggagcgcacc | 60 |
| atcttcttca | aggacgacgg | caactacaag | acccgcgccg | aggtgaagtt | cgagggcgac | 120 |
| accctggtga | accgcatcga | gctgaagggc | atcgacttca | aggaggacgg | caacatcctg | 180 |
| gggcacaagc | tggagtacaa | ctacaacagc | cacaacgtct | atatcatggc | cgacaagcag | 240 |
| aagaacggca | tcaaggtgaa | cttcaagatc | cgccacaaca | tcgaggacgg | cagcgtgcag | 300 |
| ctcgccgacc | actaccagca | gaacaccccc | atcggcgacg | gccccgtgct | gctgcccgac | 360 |
| aaccactacc | tgagctacca | gtccgccctg | agcaaagacc | ccaacgagaa | gcgcgatcac | 420 |
| atggtcctgc | tggagttcgt | gaccgccgcc | gggatcactc | tcggcatgga | cgagctgtac | 480 |
| aagagtggag | gcatgtcggc | taccgctgcc | accgtcccgc | ctgccgcccc | ggccggcgag | 540 |
| ggtggccccc | tgcacctcc | tccaaatctt | accagtaaca | ggagactgca | gcagacccag | 600 |
| gcccaggtgg | atgaggtggt | ggacatcatg | agggtgaatg | tggacaaggt | cctggagcgr | 660 |

```
gaccagaagc tatcggaact ggatgatcgc gcagatgccc tccaggcagg ggcctcccag      720
tttgaaacaa gtgcagccaa gctcaagcgc aaatactggt ggaaaaacct caagatgatg      780
atcatcttgg gagtgatttg cgccatcatc ctcatcatca tcatcgttta cttcagcact      840
taa                                                                   843
```

<210> SEQ ID NO 8
<211> LENGTH: 1812
<212> TYPE: DNA
<213> ORGANISM: Artificial Sequence
<220> FEATURE:
<223> OTHER INFORMATION: pMD0183 YFPYFPVAMP2, encoding a construct
      containing two YFP sequences

<400> SEQUENCE: 8

```
atggtgagca agggcgagga gctgttcacc ggggtggtgc ccatcctggt cgagctggac       60
ggcgacgtaa acggccacaa gttcagcgtg tccggcgagg gcgagggcga tgccacctac      120
ggcaagctga ccctgaagtt catctgcacc accggcaagc tgcccgtgcc ctggcccacc      180
ctcgtgacca ccttcggcta cggcctgcag tgcttcgccc gctaccccga ccacatgaag      240
cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctgggcac      420 aagctggagt acaactacaa cagccacaac gtctatatca tggccgacaa gcagaagaac      480
ggcatcaagg tgaacttcaa gatccgccac aacatcgagg acggcagcgt gcagctcgcc      540
gaccactacc agcagaacac ccccatcggc gacggccccg tgctgctgcc cgacaaccac      600
tacctgagct accagtccgc cctgagcaaa gaccccaacg agaagcgcga tcacatggtc      660
ctgctggagt tcgtgaccgc cgccgggatc actctcggca tggacgagct gtacaagtct      720
ggaggcaagc ttgcaatggt gagcaagggc gaggagctgt tcaccggggt ggtgcccatc      780
ctggtcgagc tggacggcga cgtaaacggc cacaagttca gcgtgtccgg cgagggcgag      840
ggcgatgcca cctacggcaa gctgaccctg aagttcatct gcaccaccgg caagctgccc      900
gtgccctggc ccaccctcgt gaccaccttc ggctacggcc tgcagtgctt cgcccgctac      960
cccgaccaca tgaagcagca cgacttcttc aagtccgcca tgcccgaagg ctacgtccag     1020
gagcgcacca tcttcttcaa ggacgacggc aactacaaga cccgcgccga ggtgaagttc     1080
gagggcgaca ccctggtgaa ccgcatcgag ctgaagggca tcgacttcaa ggaggacggc     1140
aacatcctgg gcacaagct ggagtacaac tacaacagcc acaacgtcta tatcatggcc     1200
gacaagcaga agaacggcat caaggtgaac ttcaagatcc gccacaacat cgaggacggc     1260
agcgtgcagc tcgccgacca ctaccagcag aacaccccca tcggcgacgg ccccgtgctg     1320
ctgcccgaca ccactaccct gagctaccag tccgccctga gcaaagaccc caacgagaag     1380
cgcgatcaca tggtcctgct ggagttcgtg accgccgccg ggatcactct cggcatggac     1440
gagctgtaca agagtggagg catgtcggct accgctgcca ccgtcccgcc tgccgccccg     1500
gccggcgagg gtggcccccc tgcacctcct ccaaatctta ccagtaacag agactgcag     1560 cagacccagg cccaggtgga tgaggtggtg gacatcatga gggtgaatgt ggacaaggtc     1620
ctggagcgag accagaagct atcggaactg gatgatcgcg cagatgccct ccaggcaggg     1680
gcctcccagt ttgaaacaag tgcagccaag ctcaagcgca aatactggtg gaaaaacctc     1740
```

| | |
|---|---|
| aagatgatga tcatcttggg agtgatttgc gccatcatcc tcatcatcat catcgtttac | 1800 |
| ttcagcactt aa | 1812 |

<210> SEQ ID NO 9
<211> LENGTH: 1116
<212> TYPE: DNA
<213> ORGANISM: Artificial Sequence
<220> FEATURE:
<223> OTHER INFORMATION: pMD0191, plasmid encoding a YFP-bearing construct that includes a p53 degron sequence

<400> SEQUENCE: 9

| | |
|---|---|
| atgggcaaag gttcctacgg ttccggtggc aagcttgcaa tggtgagcaa gggcgaggag | 60 |
| ctgttcaccg gggtggtgcc catcctggtc gagctggacg gcgacgtaaa cggccacaag | 120 |
| ttcagcgtgt ccggcgaggg cgagggcgat gccacctacg gcaagctgac cctgaagttc | 180 |
| atctgcacca ccggcaagct gcccgtgccc tggcccaccc tcgtgaccac cttcggctac | 240 |
| ggcctgcagt gcttcgcccg ctaccccgac cacatgaagc agcacgactt cttcaagtcc | 300 |
| gccatgcccg aaggctacgt ccaggagcgc accatcttct tcaaggacga cggcaactac | 360 |
| aagacccgcg ccgaggtgaa gttcgagggc gacaccctgg tgaaccgcat cgagctgaag | 420 |
| ggcatcgact tcaaggagga cggcaacatc ctggggcaca gctggagta caactacaac | 480 |
| agccacaacg tctatatcat ggccgacaag cagaagaacg gcatcaaggt gaacttcaag | 540 |
| atccgccaca acatcgagga cggcagcgtg cagctcgccg accactacca gcagaacacc | 600 |
| cccatcggcg acggccccgt gctgctgccc gacaaccact acctgagcta ccagtccgcc | 660 |
| ctgagcaaag accccaacga gaagcgcgat cacatggtcc tgctggagtt cgtgaccgcc | 720 |
| gccgggatca ctctcggcat ggacgagctg tacaagagtg gaggcatgtc ggctaccgct | 780 |
| gccaccgtcc cgcctgccgc cccggccggc gagggtggcc cccctgcacc tcctccaaat | 840 |
| cttaccagta acaggagact gcagcagacc caggcccagg tggatgaggt ggtgacatc | 900 |
| atgagggtga atgtggacaa ggtcctggag cgagaccaga agctatcgga actggatgat | 960 |
| cgcgcagatg ccctccaggc aggggcctcc cagtttgaaa caagtgcagc caagctcaag | 1020 |
| cgcaaatact ggtggaaaaa cctcaagatg atgatcatct gggagtgat tgcgccatc | 1080 |
| atcctcatca tcatcatcgt ttacttcagc acttaa | 1116 |

<210> SEQ ID NO 10
<211> LENGTH: 1013
<212> TYPE: DNA
<213> ORGANISM: Artificial Sequence
<220> FEATURE:
<223> OTHER INFORMATION: pMD0192, plasmid encoding a YFP-bearing construct including a SNAP-25 degron sequence

<400> SEQUENCE: 10

| | |
|---|---|
| atgggccgtg caacaaagat gctgggaagt ggttcgaatt ctggtggttc taagcttgca | 60 |
| atggtgagca agggcgagga gctgttcacc ggggtggtgc ccatcctggt cgagctggac | 120 |
| ggcgacgtaa acggccacaa gttcagcgtg tccggcgagg gcgagggcga tgccacctac | 180 |
| ggcaagctga ccctgaagtt catctgcacc accggcaagc tgcccgtgcc ctggcccacc | 240 |
| ctcgtgacca ccttcggcta cggcctgcag tgcttcgccc gctaccccga ccacatgaag | 300 |
| cagcacgact tcttcaagtc cgccatgccc gaaggctacg tccaggagcg caccatcttc | 360 |
| ttcaaggacg acacaacagc cacaacgtct atatcatggc cgacaagcag aagaacggca | 420 |

```
tcaaggtgaa cttcaagatc cgccacaaca tcgaggacgg cagcgtgcag ctcgccgacc    480
actaccagca gaacacccccc atcggcgacg gccccgtgct gctgcccgac aaccactacc   540
tgagctacca gtccgccctg agcaaagacc ccaacgagaa gcgcgatcac atggtcctgc   600
tggagttcgt gaccgccgcc gggatcactc tcggcatgga cgagctgtac aagagtggag   660
gcatgtcggc taccgctgcc accgtcccgc ctgccgcccc ggccggcgag ggtggccccc   720
ctgcacctcc tccaaatctt accagtaaca ggagactgca gcagacccag gcccaggtgg   780
atgaggtggt ggacatcatg agggtgaatg tggacaaggt cctggagcgg gaccagaagt   840
tgtcggagct ggatgaccgt gcagatgccc tccaggcagg ggcctcccag tttgaaacaa   900
gtgcagccaa gctcaagcgc aaatactggt ggaaaaacct caagatgatg atcatcttgg   960
gagtgatctg cgccatcatc ctcatcatca tcatcgttta cttcagcact taa          1013
```

```
<210> SEQ ID NO 11
<211> LENGTH: 21
<212> TYPE: PRT
<213> ORGANISM: Artificial Sequence
<220> FEATURE:
<223> OTHER INFORMATION: Peptide incorporating Bonger degron sequence

<400> SEQUENCE: 11

Lys Thr Arg Gly Val Glu Glu Val Ala Glu Gly Val Val Leu Leu Arg
1               5                   10                  15

Arg Arg Gly Asn Lys
            20

<210> SEQ ID NO 12
<211> LENGTH: 26
<212> TYPE: PRT
<213> ORGANISM: Artificial Sequence
<220> FEATURE:
<223> OTHER INFORMATION: Peptide incorporating TAZ degron

<400> SEQUENCE: 12

Lys Pro Phe Leu Asn Gly Gly Pro Tyr His Ser Arg Glu Gln Ser Thr
1               5                   10                  15

Asp Ser Gly Leu Gly Leu Gly Ser Tyr Lys
            20                  25

<210> SEQ ID NO 13
<211> LENGTH: 24
<212> TYPE: PRT
<213> ORGANISM: Artificial Sequence
<220> FEATURE:
<223> OTHER INFORMATION: Peptide incorporating HIF-alpha degron

<400> SEQUENCE: 13

Ala Ser Ala Asp Leu Asp Leu Glu Ala Leu Ala Pro Tyr Ile Pro Ala
1               5                   10                  15

Asp Asp Asp Phe Gln Leu Arg Lys
            20

<210> SEQ ID NO 14
<211> LENGTH: 14
<212> TYPE: PRT
<213> ORGANISM: Artificial Sequence
<220> FEATURE:
<223> OTHER INFORMATION: Peptide incorporating iNOS degron
```

-continued

```
<400> SEQUENCE: 14

Lys Glu Glu Lys Asp Ile Asn Asn Val Lys Lys Thr Lys
1               5                   10

<210> SEQ ID NO 15
<211> LENGTH: 17
<212> TYPE: PRT
<213> ORGANISM: Artificial Sequence
<220> FEATURE:
<223> OTHER INFORMATION: Peptide incorporating SRC3 degron

<400> SEQUENCE: 15

Asp Val Gln Lys Ala Asp Val Ser Ser Thr Gly Gln Gly Ile Asp Ser
1               5                   10                  15

Lys

<210> SEQ ID NO 16
<211> LENGTH: 22
<212> TYPE: PRT
<213> ORGANISM: Artificial Sequence
<220> FEATURE:
<223> OTHER INFORMATION: Peptide incorporating Cyclin D1 degron

<400> SEQUENCE: 16

Lys Ala Ala Glu Glu Glu Glu Ser Leu Ala Ser Thr Pro Thr Asp Val
1               5                   10                  15

Arg Asp Val Asp Ile Lys
            20

<210> SEQ ID NO 17
<211> LENGTH: 17
<212> TYPE: PRT
<213> ORGANISM: Artificial Sequence
<220> FEATURE:
<223> OTHER INFORMATION: Peptide incorporating IFNAR1 degron

<400> SEQUENCE: 17

Lys Lys Tyr Ser Ser Gln Thr Ser Gln Asp Ser Gly Asn Tyr Ser Asn
1               5                   10                  15

Lys

<210> SEQ ID NO 18
<211> LENGTH: 23
<212> TYPE: PRT
<213> ORGANISM: Artificial Sequence
<220> FEATURE:
<223> OTHER INFORMATION: Peptide incorporating p53 degron

<400> SEQUENCE: 18

Lys Pro Leu Ser Ser Ser Val Pro Ser Gln Lys Thr Tyr Gln Gly Ser
1               5                   10                  15

Tyr Gly Phe Arg Leu Gly Lys
            20

<210> SEQ ID NO 19
<211> LENGTH: 23
<212> TYPE: PRT
<213> ORGANISM: Artificial Sequence
<220> FEATURE:
<223> OTHER INFORMATION: Peptide incorporating beta catenin degron
```

<400> SEQUENCE: 19

Lys Ala Trp Gln Gln Gln Ser Tyr Leu Asp Ser Gly Ile His Ser Gly
1               5                   10                  15

Ala Thr Thr Thr Ala Pro Lys
            20

<210> SEQ ID NO 20
<211> LENGTH: 1077
<212> TYPE: DNA
<213> ORGANISM: Artificial Sequence
<220> FEATURE:
<223> OTHER INFORMATION: pMD0185 plasmid ORF encoding for a control (no
      degron) YFP-bearing construct

<400> SEQUENCE: 20

| | |
|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccttcggcta cggcctgcag tgcttcgccc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagct accagtccgc cctgagcaaa gaccccaacg agaagcgcga tcacatggtc | 660 |
| ctgctggagt tcgtgaccgc cgccgggatc actctcggca tggacgagct gtacaagagt | 720 |
| ggaggcatgt cggctaccgc tgccaccgtc ccgcctgccg ccccggccgg cgagggtggc | 780 |
| cccccctgcac ctcctccaaa tcttaccagt aacaggagac tgcagcagac ccaggcccag | 840 |
| gtggatgagg tggtggacat catgagggtg aatgtggaca aggtcctgga gcgrgaccag | 900 |
| aagctatcgg aactggatga tcgcgcagat gccctccagg caggggcctc ccagtttgaa | 960 |
| acaagtgcag ccaagctcaa cgcaaatac tggtggaaaa acctcaagat gatgatcatc | 1020 |
| ttgggagtga tttgcgccat catcctcatc atcatcatcg tttacttcag cacttaa | 1077 |

<210> SEQ ID NO 21
<211> LENGTH: 1077
<212> TYPE: DNA
<213> ORGANISM: Artificial Sequence
<220> FEATURE:
<223> OTHER INFORMATION: pMD0185 ORF encoding for a control/common
      EFP-bearing construct

<400> SEQUENCE: 21

| | |
|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccctgacctg gggcgtgcag tgcttcagcc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |

```
gtgaaccgca tcgagctgaa gggcatcgac ttcaaggagg acggcaacat cctggggcac       420
aagctggagt acaactacat cagccacaac gtctatatca ccgccgacaa gcagaagaac       480
ggcatcaagg ccaacttcaa gatccgccac aacatcgagg acggcagcgt gcagctcgcc       540
gaccactacc agcagaacac ccccatcggc gacggccccg tgctgctgcc cgacaaccac       600
tacctgagca cccagtccgc cctgagcaaa gaccccaacg agaagcgcga tcacatggtc       660
ctgctggagt tcgtgaccgc cgccgggatc actctcggca tggacgagct gtacaagagt       720
ggaggcatgt cggctaccgc tgccaccgtc ccgcctgccg cccggccgg cgagggtggc        780 cccctgcac ctcctccaaa tcttaccagt aacaggagac tgcagcagac ccaggcccag        840
gtggatgagg tggtggacat catgagggtg aatgtggaca aggtcctgga gcgrgaccag       900
aagctatcgg aactgaataa tcgcgcaaat gccctccagg caggggcctc cgtgtttgaa       960
acaagtgcag ccaagctcaa gcgcaaatac tggtggaaaa acctcaagat gatgatcatc      1020
ttgggagtga tttgcgccat catcctcatc atcatcatcg tttacttcag cacttaa        1077

<210> SEQ ID NO 22
<211> LENGTH: 1122
<212> TYPE: DNA
<213> ORGANISM: Artificial Sequence
<220> FEATURE:
<223> OTHER INFORMATION: pMD0189 ORF encoding for a YFP-bearing
      construct having a Bonger degron sequence

<400> SEQUENCE: 22
atgggcaaac gtcgccgtgg taacaaatcc ggtggcaagc ttgcaatggt gagcaagggc        60
gaggagctgt tcaccggggt ggtgcccatc ctggtcgagc tggacggcga cgtaaacggc       120
cacaagttca gcgtgtccgg cgagggcgag ggcgatgcca cctacggcaa gctgaccctg       180
aagttcatct gcaccaccgg caagctgccc gtgccctggc ccaccctcgt gaccaccttc       240
ggctacggcc tgcagtgctt cgcccgctac cccgaccaca tgaagcagca cgacttcttc       300
aagtccgcca tgcccgaagg ctacgtccag gagcgcacca tcttcttcaa ggacgacggc       360
aactacaaga cccgcgccga ggtgaagttc gagggcgaca cccctggtgaa ccgcatcgag      420 ctgaagggca tcgacttcaa ggaggacggc aacatcctgg gcacaagct ggagtacaac       480 tacaacagcc acaacgtcta tatcatggcc gacaagcaga agaacggcat caaggtgaac      540
ttcaagatcc gccacaacat cgaggacggc agcgtgcagc tcgccgacca ctaccagcag      600
aacaccccca tcggcgacgg ccccgtgctg ctgcccgaca accactacct gagctaccag      660
tccgccctga gcaaagaccc caacgagaag cgcgatcaca tggtcctgct ggagttcgtg      720
accgccgccg ggatcactct cggcatggac gagctgtaca agagtggagg catgtcggct      780
accgctgcca ccgtcccgcc tgccgccccg gccggcgagg tggcccccc tgcacctcct      840 ccaaatctta ccagtaacag gagactgcag cagacccagg cccaggtgga tgaggtggtg      900
gacatcatga gggtgaatgt ggacaaggtc ctggagcgag accagaagct atcggaactg      960
gataatcgcg cagatgccct ccaggcaggg gcctcccagt ttgaaacaag tgcagccaag     1020
ctcaagcgca atactggtg gaaaaacctc aagatgatga tcatcttggg agtgatttgc     1080
gccatcatcc tcatcatcat catcgtttac ttcagcactt aa                        1122

<210> SEQ ID NO 23
<211> LENGTH: 1122
<212> TYPE: DNA
<213> ORGANISM: Artificial Sequence
<220> FEATURE:
```

<223> OTHER INFORMATION: pMD0190 ORF encoding for a YFP-bearing
      construct having an iNOS degron sequence

<400> SEQUENCE: 23

```
atgggcaaag atattaataa caataaatcc ggtggcaagc ttgcaatggt gagcaagggc      60
gaggagctgt tcaccggggt ggtgcccatc ctggtcgagc tggacggcga cgtaaacggc     120
cacaagttca gcgtgtccgg cgagggcgag ggcgatgcca cctacggcaa gctgaccctg     180
aagttcatct gcaccaccgg caagctgccc gtgccctggc ccaccctcgt gaccaccttc     240
ggctacggcc tgcagtgctt cgcccgctac cccgaccaca tgaagcagca cgacttcttc     300
aagtccgcca tgcccgaagg ctacgtccag gagcgcacca tcttcttcaa ggacgacggc     360
aactacaaga cccgcgccga ggtgaagttc gagggcgaca ccctggtgaa ccgcatcgag     420
ctgaagggca tcgacttcaa ggaggacggc aacatcctgg ggcacaagct ggagtacaac     480
tacaacagcc acaacgtcta tatcatggcc gacaagcaga gaacggcat caaggtgaac      540 ttcaagatcc gccacaacat cgaggacggc agcgtgcagc tcgccgacca ctaccagcag     600
aacaccccca tcggcgacgg ccccgtgctg ctgcccgaca accactacct gagctaccag     660
tccgccctga gcaaagaccc caacgagaag cgcgatcaca tggtcctgct ggagttcgtg     720
accgccgccg ggatcactct cggcatggac gagctgtaca agagtggagg catgtcggct     780
accgctgcca ccgtcccgcc tgccgccccg gccggcgagg gtggcccccc tgcacctcct     840
ccaaatctta ccagtaacag gagactgcag cagacccagg cccaggtgga tgaggtggtg     900
gacatcatga gggtgaatgt ggacaaggtc ctggagcgag accagaagct atcggaactg     960
gatgatcgcg cagatgccct ccaggcaggg gcctcccagt ttgaaacaag tgcagccaag    1020
ctcaagcgca aatactggtg gaaaaacctc aagatgatga tcatcttggg agtgatttgc    1080
gccatcatcc tcatcatcat catcgtttac ttcagcactt aa                       1122
```

ASSAY WITH SYNAPTOBREVIN BASED MOIETY

This application claims the benefit of U.S. Provisional Application No. 62/404,513, filed on Oct. 5, 2016, and U.S. Provisional Application No. 62/336,964, filed May 16, 2016. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is characterization of botulinum neurotoxins using cell based assays, particularly botulinum serotype B neurotoxin.

BACKGROUND

The following description includes information that may be useful in understanding the present invention. It is not an admission that any of the information provided herein is prior art or relevant to the presently claimed invention, or that any publication specifically or implicitly referenced is prior art.

Botulinum neurotoxins (BoNTs) are extremely toxic proteins and can be classified into distinct subgroups based, inter alia, on peptide sequence and/or substrate specificity. All of the naturally occurring BoNTs (BoNT/A-G) are composed of a heavy chain that mediates toxin entry into a target cell and a light chain with zinc-dependent protease activity that hydrolyzes selected SNARE proteins that mediate fusion of neurotransmitter vesicles to the membrane that forms part of the synaptic cleft.

For example, the light chain of BoNT/A hydrolyzes with high specificity SNAP-25, which is required for vesicle-mediated exocytosis of acetylcholine into the synaptic cleft. Known assays for such hydrolytic activity include those described in PCT Application Publication No. WO 2009/035476, to Fish and Dong, which describes the use of a peptide construct that includes a fluorophore and a quencher that are covalently linked to the respective ends of a SNAP-25 sequence. All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. Cleavage by BoNT/A (or other BoNTs with a substrate specificity towards SNAP-25) result in physical separation of the cleavage products and so reduce fluorescence quenching, which can then be quantified. Among other choices, it is often preferred that such assay is performed as an in vitro solid-phase based assay.

While such an assay is conceptually straightforward and can be used characterize BoNT/A, BoNT/C, or BoNT/E activity, such an assay cannot simply be modified to a cell-based assay for determination of BoNT/B activity by replacing the SNAP-25 motif with a SNARE domain, as the corresponding SNARE domain includes a membrane spanning sub-domain that would place an N-terminal fluorophore on the interior of a vesicle (thereby preventing energy transfer). In such case, only diffusion of the fluorescence signal would be observed (Dong et al. PNAS (2004), Vol. 101, No. 41, 14701-14706; United States Patent Publication No. 2006/0134722, to Chapman and Dong).

Other cell-based assays for botulinum neurotoxins are described in United States Patent Application Publication No. 2012/0322092 (to Tucker and Zeytin), and U.S. Pat. No. 9,274,121 (to Atapattu and Tucker). Cells utilized in such assays incorporate reporting constructs that include fluorescent peptide regions and botulinum neurotoxin (BoNT) substrate peptide regions, and are used to quantify BoNTs utilized as pharmaceutical compounds. In such cell-based assays reporting constructs expressed within the cells undergo measurable changes (for example, changes in the intensity or distribution of observed fluorescence) when exposed to an appropriate proteolytic activity. Such assays can utilize FRET to provide a fluorescence signal, or utilize detection of non-FRET mediated fluorescence (or the lack thereof) following degradation of the construct following cleavage by the botulinum neurotoxin. In such approaches, however, excessive persistence in the fluorescent emission of a fluorescent peptide following lysis of a reporting construct by a proteolytic enzyme can interfere with the results of the assays.

Approaches have been suggested to modulate the degree to which such reporting constructs are degraded within cells. Such approaches typically involve the insertion of degrons (i.e. short peptide sequences that increase the rate of degradation of a protein containing such sequences). For example, United States Patent Application Publication No. 2015/0010931 (to Oyler and Tsai) discusses application of the N-end rule to increase the rate of degradation of a product of proteolysis of a reporting construct. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. In such a construct the protease substrate peptide region is positioned near the N-terminus of the reporting construct and a fluorescent peptide region is positioned near the C-terminus. The protease substrate peptide sequence is selected so that proteolysis exposes an N-terminal amino acid associated with increased degradation rate, following the "N-end rule", leading to an increased rate of degradation for the fluorescent peptide. Oyler and Tsai teach the use of a substrate peptide region that is, essentially, a fragment of the substrate of the light chain of the BoNT expressed by serotype A *Clostridium botulinum*. United States Patent Application 2006/105953 (to LaCoste and Evans) teaches a similar reporting construct where the substrate peptide region is a caspase substrate. Such approaches, however, limit the selection of proteases and substrate peptide regions to sequences that provide the requisite N-terminal amino acid.

U.S. Pat. No. 9,249,449 (to Miyawaki and Hirano) discuss an alternative design for a reporting construct, in which an N-terminal fluorescent peptide is separate from a second fluorescent peptide by a proteolysis-terminating peptide, followed by a degradation-susceptible peptide positioned near the C-terminus. Degradation starting at the C-terminus, which can be mediated by the presence of a degron sequence, results in loss of the second fluorescent peptide and a measurable change in the observed fluorescence. Such an approach, however, limits reporting constructs to those that are degraded by specific intracellular mechanisms that respond to proteolysis-terminating peptide sequences.

Therefore, there is still a need for improved BoNT assays, and especially cell-based assays for BoNTs that cleave synaptobrevin.

SUMMARY OF THE INVENTION

The inventive subject matter provides compositions and methods for cell-based assays for specific protease activities, in particular botulinum neurotoxins. A pair of peptide constructs is provided where at least one of the pair incorporates a cleavage site for the protease activity. The pair of peptide constructs include sequences that provide co-localization of the members of the pair and detectable labels (e.g. peptides derived from GFP or GFP mutants). Cleavage results in release of detectable label, followed by degradation of the released label. Peptide constructs can include sequences that enhance or increase the rate of this degradation, for example degron sequences. In some embodiments one member of the pair of peptide constructs includes mutations that prevent or reduce the rate of cleavage by the specific protease activity, leading to retention of an associated label. Such a retained or otherwise non-labile label can be used for data normalization.

One embodiment of the inventive concept is a reporting construct for characterizing botulinum serotype neurotoxin that includes a first reporter peptide having a first membrane binding peptide configured to localize to a vesicle membrane, a first fluorescent peptide, and a first linking peptide derived from synaptobrevin positioned between the first membrane binding peptide and the first fluorescent peptide, and also a second reporter peptide having a second membrane binding peptide configured to localize to a vesicle membrane, a second fluorescent peptide, and a second linking peptide derived from synaptobrevin positioned between the second membrane binding peptide and the second fluorescent peptide. In such a construct the first fluorescent peptide and the second fluorescent peptide (which can be derived from GFP or a GFP mutation) are positioned such that no useful (e.g. less than about 5%) Forster resonance energy transfer (FRET) occurs between them. Such peptides can be encoded on a single plasmid, or can be encoded on separate and distinct plasmids. In some embodiments the first linking region incorporates one or more mutations that decrease susceptibility to proteolysis by botulinum B neurotoxin, for example a point mutation of an amino acid that forms part of a botulinum serotype B neurotoxin cleavage site and/or an exosite of synaptobrevin (e.g. D64N, D65N, D68N, and Q76V mutations of synaptobrevin). In some embodiments the first fluorescent peptide and the second fluorescent peptide have distinguishably different emission frequencies. In such embodiments the reporting constructs the first fluorescent peptide and/or the second fluorescent peptide can include one or more mutations that increase the rate of intracellular proteolysis relative to an analogous peptide that does not incorporate the one or more mutations. Examples of suitable mutations include a point mutation that replaces a native amino acid with a basic amino acid and inclusion of a degron sequence. Such reporting constructs can be expressed in a cell, such as a Neuro2A cell, M17 cell, PC12 cell, SK-N-SH cell, LNCaP cell, an immortalized murine astrocyte, a human and/or murine hTERT immortalized cell, an iPSC neuron, a stem cell derived neuron, and/or a primary neuron.

Another embodiment of the inventive concept is a method for characterizing an analyte (such as a botulinum neurotoxin) by (1) providing a field comprising a plurality of spatially distinct testing regions (for example, a population of cells), (2) obtaining a first image of the field prior to exposure to the analyte, where the first image provides a measure of intensity of a first signal, (3) identifying (within the first image) one or more of the spatially distinct testing regions wherein the intensity of the first signal lies within a range delimited by a designated minimum value and a designated maximum value, (4) generating a quantitation mask representing one or more areas within the image delimited by the minimum value and the maximum value, (5) recording a first intensity value within an area of the first image defined by the quantitation mask, (6) contacting the field with a sample containing the analyte, (7) obtaining a second image of the field, (8) recording a second intensity value within an area of the second image defined by the quantitation mask, (9) generating a first result by combining the first intensity value with total area represented by the quantitation mask, (10) generating a second result by combining the second intensity value with total area represented by the quantitation mask, and (11) comparing the second result with the first result. In such a method the first result can be obtained by multiplying the first intensity value by total area represented by the quantitation mask and the second result can be obtained by multiplying the second intensity value by total area represented by the quantitation mask. Examples of cells suitable for this purpose include Neuro2A cells, M17 cells, PC12 cells, SK-N-SH cells, LNCaP cells, immortalized murine astrocytes (for example, SV40T cells), human and/or murine hTERT immortalized cells, iPSC neurons, stem cell derived neurons, and/or primary neurons. In some embodiments the minimum value represents a minimum fluorescence intensity that is distinguishable from background fluorescence. Similarly, the maximum value can represents a value characteristic of saturation of a detection device utilized to acquire the first image, or can represent a value beyond which a detection device utilized to acquire the first image departs from linearity between detection device response and light intensity.

Another embodiment of the inventive concept is a reporting peptide construct that has an N-terminus and a C-terminus, a degron positioned at or near the N-terminus, a localization sequence positioned at or near the C-terminus of the reporting peptide, a signaling sequence positioned proximal to the degron, and a protease substrate sequence positioned between the signaling sequence and the localization sequence. In such a reporting construct the localization sequence is selected to localize the reporting peptide in a protected region of a cell. Suitable degron sequences include an amino acid selected according to the N-end rule and degrons associated with peptides such as Bonger (SEQ ID NO. 11), TAZ (SEQ ID NO. 12), HIF-α (SEQ ID NO. 13), iNOS (SEQ ID NO. 14), SRC3 (SEQ ID NO. 15), Cyclin D1 (SEQ ID NO. 16), IFNAR1 (SEQ ID NO. 17), p53 (SEQ ID NO. 18), β-catenin (SEQ ID NO. 19), and SNAP-25 (SEQ ID NO. 10). In such embodiments the localization sequence can be selected to localize the reporting peptide at a membrane (e.g. a plasma membrane, a rough ER membrane, a smooth ER membrane, a vesicle membrane, and/or a nuclear membrane) and can be a part of or include a protease substrate sequence (and/or cleavage site), for example a BoNT substrate protein. In some embodiments the signaling sequence includes a fluorescent peptide sequence, for example a peptide sequence that has at least 80% sequence identity to green fluorescent protein (GFP). In some embodiments the protease substrate sequence comprises all or a portion of a BoNT substrate sequence, for example a BoNT/A substrate sequence, a BoNT/B substrate sequence, a BoNT/C substrate sequence, a BoNT/D substrate sequence, a BoNT/E substrate sequence, a BoNT/F substrate sequence, and a BoNT/G substrate sequence.

Another embodiment of the inventive concept is a cell (such as a neuron or neuronally-derived cell) that incorporates a reporting peptide construct that has an N-terminus and a C-terminus, a degron positioned at or near the N-terminus, a localization sequence positioned at or near the C-terminus of the reporting peptide and is selected to localize the reporting peptide in a protected region of the cell, a signaling sequence positioned proximal to the degron, and a protease substrate sequence positioned between the signaling sequence and the localization sequence. In such a reporting construct the localization sequence is selected to localize the reporting peptide in a protected region of a cell. Suitable degron sequences include an amino acid selected according to the N-end rule and degrons associated with peptides such as Bonger (SEQ ID NO. 11), TAZ (SEQ ID NO. 12), HIF-α (SEQ ID NO. 13), iNOS (SEQ ID NO. 14), SRC3 (SEQ ID NO. 15), Cyclin D1 (SEQ ID NO. 16), IFNAR1 (SEQ ID NO. 17), p53 (SEQ ID NO. 18), β-catenin (SEQ ID NO. 19), and SNAP-25 (SEQ ID NO. 10). In such embodiments the localization sequence can be selected to localize the reporting peptide at a membrane (e.g. a plasma membrane, a rough ER membrane, a smooth ER membrane, a vesicle membrane, and/or a nuclear membrane) and can be a part of or include a protease substrate sequence (and/or cleavage site), for example a BoNT substrate protein. In some embodiments the signaling sequence includes a fluorescent peptide sequence, for example a peptide sequence that has at least 80% sequence identity to green fluorescent protein (GFP). In some embodiments the protease substrate sequence comprises all or a portion of a BoNT substrate sequence, for example a BoNT/A substrate sequence, a BoNT/B substrate sequence, a BoNT/C substrate sequence, a BoNT/D substrate sequence, a BoNT/E substrate sequence, a BoNT/F substrate sequence, and a BoNT/G substrate sequence.

Another embodiment of the inventive concept is a method of characterizing an analyte (for example, a botulinum neurotoxin or BoNT) by (1) obtaining a cell comprising a reporting construct having an N-terminus and a C-terminus, a degron positioned at or near the N-terminus of the reporting peptide, a localization sequence positioned at or near the C-terminus of the reporting peptide, a signaling sequence positioned proximal to the degron, and a protease substrate sequence positioned between the signaling sequence and the localization sequence, where the localization sequence is selected to localize the reporting peptide in a protected region of the cell, (2) contacting the cell with the analyte, wherein presence of the analyte results in an intracellular proteolytic activity within the cell that is directed towards the protease substrate sequence, and (3) obtaining a signal from the signaling sequence. In such an embodiment the degron can include an amino acid selected according to the N-end rule and/or a degron sequence derived from Bonger (SEQ ID NO. 11), TAZ (SEQ ID NO. 12), HIF-α (SEQ ID NO. 13), iNOS (SEQ ID NO. 14), SRC3 (SEQ ID NO. 15), Cyclin D1 (SEQ ID NO. 16), IFNAR1 (SEQ ID NO. 17), p53 (SEQ ID NO. 18), β-catenin (SEQ ID NO. 19), and SNAP-25 (SEQ ID NO. 10). In such a method the localization sequence can be selected to localize the reporting peptide at a membrane, such as a plasma membrane, a rough ER membrane, a smooth ER membrane, a vesicle membrane, and/or a nuclear membrane, and can be part of or include the protease substrate sequence (for example, a BoNT substrate protein). Suitable protease substrate sequences include a BoNT/A substrate sequence, a BoNT/B substrate sequence, a BoNT/C substrate sequence, a BoNT/D substrate sequence, a BoNT/E substrate sequence, a BoNT/F substrate sequence, and a BoNT/G substrate sequence. In such embodiments the signaling sequence can be a fluorescent peptide sequence, for example a peptide having at least 80% sequence identity to green fluorescent protein.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIGS. 6A to 6H depict the structures of various peptide constructs of the inventive concept. FIG. 6A shows a pMD0032 ORF encoding a YFP-synaptobrevin (VAMP2) peptide (SEQ ID NO. 1). FIG. 6A is divided into FIG. 6A-A and FIG. 6A-B. FIG. 6B shows a pMD0034 ORF encoding a CFP-synaptobrevin (VAMP2) peptide (SEQ ID NO. 2). FIG. 6B is divided into FIG. 6B-A and FIG. 6B-B. FIG. 6C shows a different pMD0034 ORF, encoding a YFP-synaptobrevin (VAMP2) peptide (SEQ ID NO. 3). FIG. 6C is divided into FIG. 6C-A and FIG. 6C-B. FIG. 6D shows a pMD0071 ORF encoding for a CFP-synaptobrevin (VAMP2) peptide (SEQ ID NO. 4). FIG. 6D is divided into FIG. 6D-A and FIG. 6D-B. FIG. 6E shows a different pMD0071 ORF, encoding for a YFP-synaptobrevin (VAMP2) peptide (SEQ ID NO. 5). FIG. 6E is divided into FIG. 6E-A and FIG. 6E-B. FIG. 6F shows a pMD0183 ORF encoding for a YFP-YFP-synaptobrevin (VAMP2) peptide (SEQ ID NO. 8), which incorporates two YFP peptides arranged sequentially. FIG. 6F is divided into FIG. 6F-A, FIG. 6F-B, FIG. 6F-C, and FIG. 6F-D. FIG. 6G shows a pMD0185 ORF encoding for a CFP-synaptobrevin (VAMP2) peptide (SEQ ID NO. 6). FIG. 6G is divided into FIG. 6G-A and FIG. 6G-B. FIG. 6H shows a different pMD0185 ORF, encoding for a YFP-synaptobrevin (VAMP2) peptide (SEQ ID NO. 7). FIG. 6H is divided into FIG. 6H-A and FIG. 6H-B.

FIG. 8A shows a reporting construct pair that does not include a degron sequence position towards the N-terminus relative to a reporting fluorophore (e.g. YFP). FIG. 8B shows a reporting construct pair that includes a degron sequence position towards the N-terminus relative to a reporting fluorophore (e.g. YFP).

FIG. 9A provides a photomicrograph of cells expressing a control (i.e. no degron sequence) reporting construct pair in the presence and absence of BoNT/B. FIG. 9B shows the overall fluorescence emission from cells such as those shown in FIG. 9A as characterized using a fluorescence plate reader.

FIG. 10A shows measurements of YFP emission in the presence and absence of BoNT/B. FIG. 10B shows measurements of CFP emission in the presence and absence of BoNT/B. FIG. 10C shows results of measurements of YFP fluorescence:CFP fluorescence ratio in the presence and absence of BoNT/B.

FIG. 11A shows measurements of YFP emission in the presence and absence of BoNT/B. FIG. 11B shows measurements of CFP emission in the presence and absence of BoNT/B. FIG. 11C shows results of measurements of YFP fluorescence:CFP fluorescence ratio in the presence and absence of BoNT/B.

FIGS. 12A and 12B provide photomicrographs obtained from cells transformed with a control reporting construct pair that does not include a degron sequence and from cells transformed with reporting constructs that include a degron sequence. FIG. 12A shows brightfield, YFP emission, and CFP emission photomicrographs of transformed cells expressing a control reporting construct pair (containing no degron sequence) and transformed cells expressing reporting construct pairs that include degron sequences (specifically, Bonger or iNOS degron sequences) positioned N-terminally to the YFP peptide of the YFP-bearing member of the reporting construct pair. FIG. 12B shows the results of studies similar to those shown in FIG. 12A, but performed using cells carrying either the pMD0191 or pMD0192 reporting construct pairs, both of which show improved dynamic range on exposure to BoNT/B relative to control cell.

DETAILED DESCRIPTION

Figure 2:
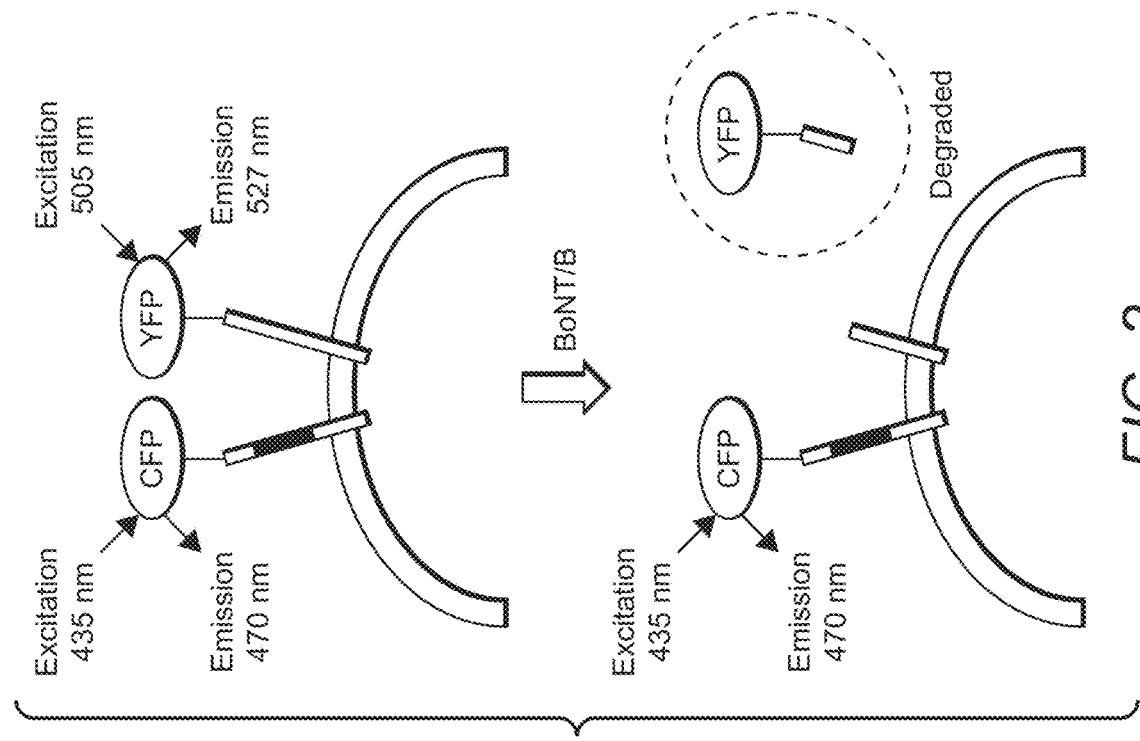
FIG. 2 shows an example of a reporting construct pair of the inventive concept.

The inventive subject matter provides compositions and methods in which reporting constructs and quantitation methods are described that are useful in characterizing botulinum B neurotoxin (BoNT/B) using cell based assays. Cells are transformed, either transiently or permanently to express a reporting construct that includes one or more fluorescing peptide domains. In instances where two or more fluorescing peptide domains are provided, they are arranged so that no useful Forster resonance energy transfer (FRET) occurs between fluorescing peptides (i.e. less than 25%, 20%, 15%, 10%, 5%, 2.5%, or 1% energy transfer). Such reporting constructs include a membrane targeting region derived from synaptobrevin, which is selective for vesicle membranes, thereby anchoring the reporting construct to a vesicle. A cleavage and recognition site that serves as a BoNT/B substrate is positioned such that BoNT/B light chain activity releases one or more fluorescent peptide portions of the reporting construct into the cytosol. Such reporting constructs are expressed in cells that include cell surface receptors that facilitate uptake of BoNT/B, and the resulting changes in fluorescence observed in such cells on exposure to BoNT/B can be utilized in characterization of the neurotoxin.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

A reporting construct of the inventive construct can incorporate one or more amino acids or amino acid sequences (e.g. degron sequences) that enhance degradation of at least a portion of the reporting construct. For example, a reporting construct can include one or more degron sequence(s) positioned at or near the N-terminus of the reporting construct. A reporting peptide construct can, for example, produce a detectable signal (for example, a fluorescent peptide) from a region that is positioned adjacent to a degron sequence and is interposed between the degron sequence and a protease substrate sequence (which can be positioned at or near the C-terminus of the reporting construct). Such a protease substrate sequence can include one or more protease recognition sequences, one or more protease cleavage sites (which can be distinct from or essentially to the protease recognition sequences), and/or a localization sequence.

Alternatively, a localization sequence can be provided that is distinct from the protease substrate sequence and positioned between the protease substrate sequence and the C terminus of the reporting construct. Such a localization sequence serves to localize the intact reporting construct in a protected site, within which a reporting construct is protected or at least partially protected from an intracellular protein degradation system that interacts with a degron sequence of the reporting construct. On exposure to the protease activity being characterized a cleavage event occurs within the protease substrate sequence, release a fragment of the reporting construct that includes the degron sequence and the reporting peptide sequence from the protected site. Release from the protected site results in rapid degradation of the reporting peptide sequence (i.e. occurring at an elevated rate relative to the reporting sequence alone within the same intracellular environment), resulting in a rapid change in the observed detectable signal.

One should appreciate that the disclosed techniques provide many advantageous technical effects including providing highly sensitive testing for characterization of BoNT/B neurotoxin that provides a high degree of correlation to animal-based testing while relying on cultured cells. In addition, the disclosed methods and compositions provide reduced interference in such cell-based assay results from released, but undegraded, fragments of the reporting construct. This reduced interference can improve sensitivity and/or reduce time to first result in a cell-based assay.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Figure 1:
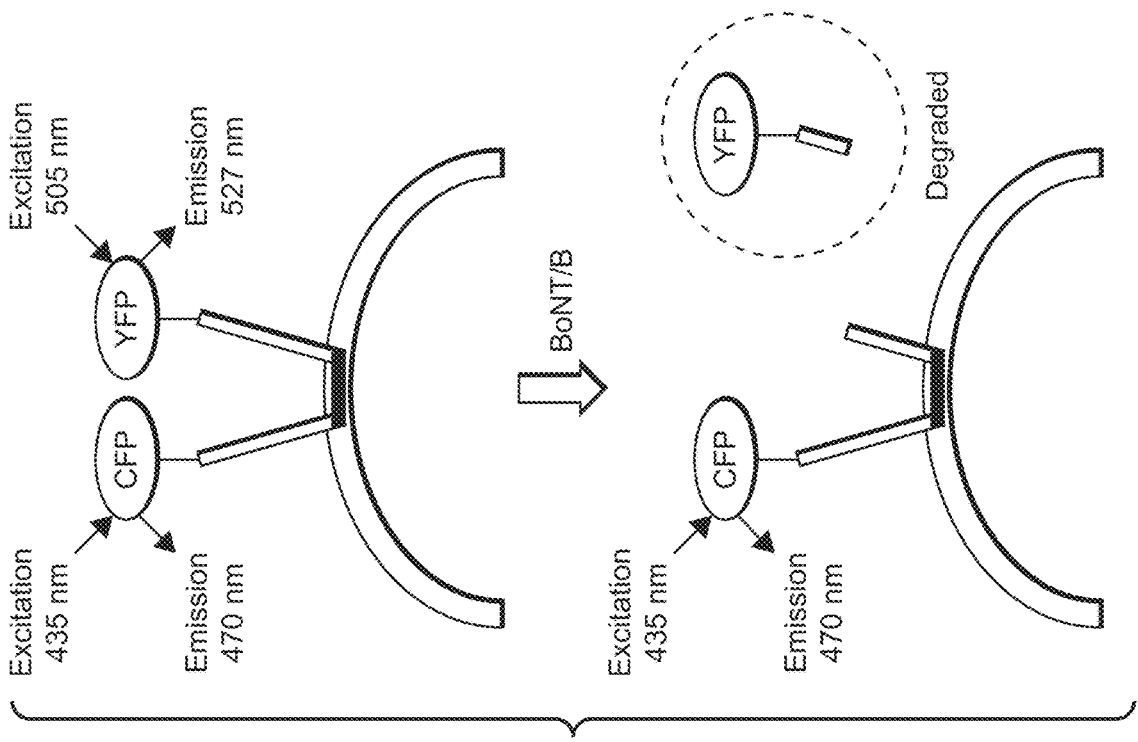
FIG. 1 shows an exemplary arrangement of the components of a reporting construct of the inventive concept.

One embodiment of the inventive concept is a reporting construct arranged as a single peptide that includes a first fluorescent peptide region, a synaptobrevin derived membrane binding region, a BoNT/B recognition and cleavage site, and a second fluorescent peptide. The first and second fluorescent peptide can have distinct excitation and emission spectra, and are arranged so that no significant FRET occurs between them. In a preferred embodiment the BoNT/B recognition and cleavage site is derived from synaptobrevin. Cleavage of the recognition and cleavage site results in release of one of the fluorescent peptides into the cytosol, where it can be subsequently degraded. In some embodiments one or both of the fluorescent peptides can include amino acid sequence modifications (such as incorporation of basic amino acids and/or degron sequences) that enhance degradation of the released peptide fragment on release into the cytosol. FIG. 1 shows an exemplary arrangement of the components of such a reporting construct.

In a preferred embodiment of the inventive concept a fluorescent peptide utilized in the construct is derived from green fluorescent protein (GFP) or a GFP mutation. Suitable GFP mutations include EGFP, EBFP, EBFP2. Azurite, mKalamal, CFP, ECFP, Cerulean, CyPet, mTurqoise, YFP, Citrine, Venus, and/or YPet. It should be appreciated that in some embodiments one member of the fluorescent peptide pair can be retained on the vesicle membrane on exposure of a cell expressing the construct to BoNT/B. In embodiments where one of the fluorescent peptides is retained on the vesicle membrane following proteolysis by BoNT/B light chain (or otherwise not degraded following exposure of the cell to a BoNT), emission measurement from the retained fluorescent peptide can be used to normalize emission measurements made from the release fluorescent peptide. For example, fluorescence emission from such a retained fluorescent peptide can be used to normalize results for differences in gene expression, cell number, and/or cell distribution within different test sites or test wells of an assay test fixture (such as a multiwell test plate). Alternatively, fluorescence emission from such a retained fluorescent peptide can be utilized as an identifying feature in an artificial vision system, for example an artificial vision system utilizing an algorithm that identifies specific features of interest (e.g. labeled cell and/or intracellular components) within an image obtained from a test area. In embodiments where both fluorescent peptides are released from the vesicle membrane by the action of BoNT/B light chain proteolytic activity data, similar normalization can be provided by the application of a reference dye (for example, a fluorescent cell membrane-binding dye with a distinguishable excitation and emission spectra).

In another embodiment of the inventive concept a pair of reporting constructs are utilized. In such an embodiment each member of the pair includes a synaptobrevin-derived membrane binding portion and a fluorescent peptide, with each member of the pair carrying a distinct fluorescent peptide. One member of the peptide pair includes a BoNT/B cleavage and recognition site (such as synaptobrevin or a synaptobrevin-derived peptide) interposed between the membrane binding portion and the fluorescent peptide. The remaining member of the peptide pair includes a peptide that is interposed between the membrane binding portion and the fluorescent peptide, but that does not act as a BoNT/B recognition and cleavage site. Such a peptide can be, for example, synaptobrevin or a synaptobrevin-derived peptide which includes amino acid substitutions at the BoNT/B proteolytic cleavage site and/or outlying BoNT/B recognition sites (e.g. exosites). As a result such a member of the peptide pair can retain localization, complex formation, and other characteristics of synaptobrevin, but is not cleaved by BoNT/B activity. As a result the associated fluorophore is retained on the vesicle membrane. It should be appreciated that, unlike BoNT peptides such as those reported in U.S. Pat. No. 9,624,529 (to Oyler and Tsai), use of such peptide pairs incorporating a non-cleavable member provides for an internal control useful in data normalization. In some embodiments significant (i.e. greater than 5% energy transfer) can occur between the fluorophores of a reporting construct pair. In other embodiments, while the different fluorescent peptides of the reporting construct can have distinct excitation and emission spectra the pair of fluorescent peptides is arranged such that no significant FRET occurs between them. It should be appreciated that such a lack of significant (i.e. greater than 5%) energy transfer between the fluorescent peptide can reduce or eliminate quenching effects associated with FRET, which in turn can improve the utility of a signal obtained from a retained (or otherwise non-labile) fluorescent peptide for data normalization. Cleavage of the BoNT/B recognition and cleavage site results in the release of one of the fluorescent peptides into the cytosol, where it is subsequently degraded. As noted above, such a released fluorescent peptide can be associated with amino acids and or amino acid sequences that enhance the rate of degradation on release into the cytosol (relative to a corresponding peptide that lacks a degradation-enhancing amino acid or amino acid sequence). FIG. 2 shows an example of such a reporting construct pair.

Figure 3:
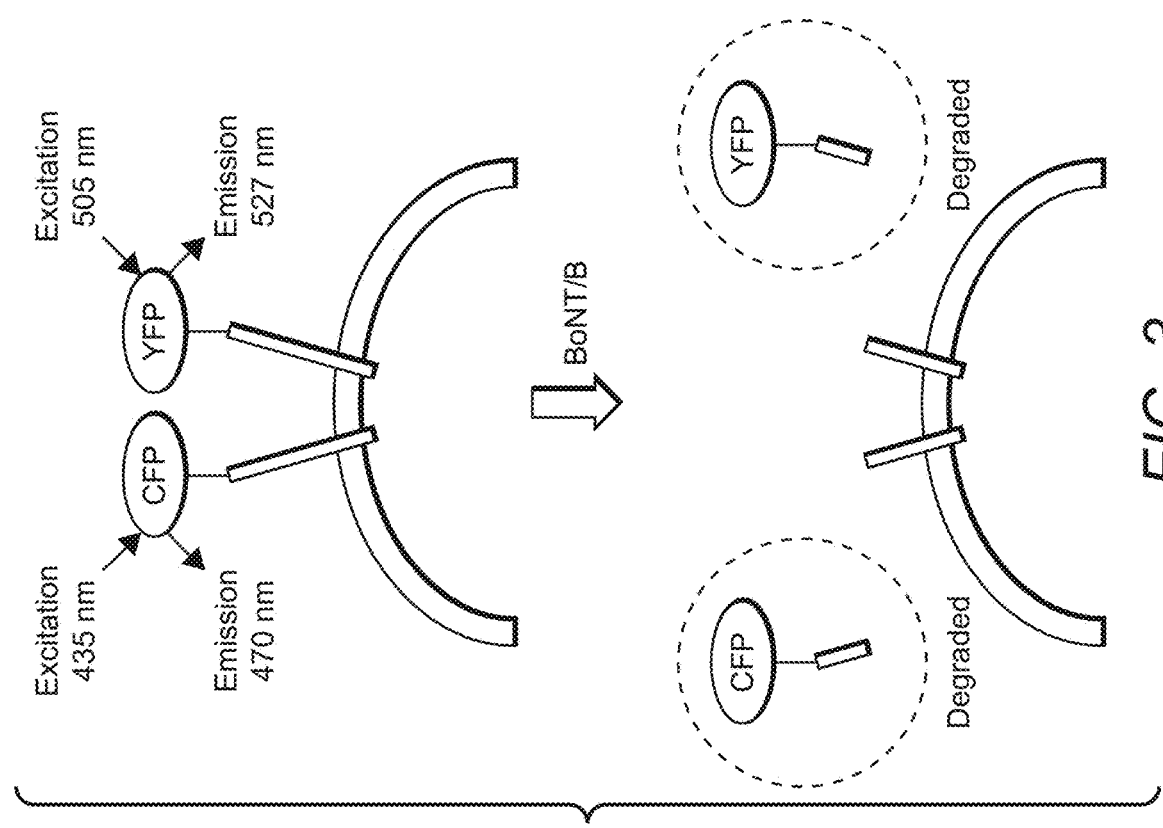
FIG. 3 shows another example of a reporting construct pair of the inventive concept.

In another embodiment of the inventive concept a pair of reporting constructs are utilized. In such an embodiment each member of the pair includes a synaptobrevin-derived (i.e. corresponding to a portion of the synaptobrevin amino acid sequence and/or having greater than about 80% sequence identity with synaptobrevin) membrane binding portion, a BoNT/B recognition and cleavage site (for example, synaptobrevin or a synaptobrevin-derived peptide) and a fluorescent peptide, with each member of the pair carrying a distinct fluorescent peptide. One member of the peptide pair includes a BoNT/B cleavage and recognition site (such as synaptobrevin or a synaptobrevin-derived peptide) interposed between the membrane binding portion and the fluorescent peptide. While the distinct fluorescent peptides can have distinct excitation and emission spectra, the construct pair is arranged such that no significant FRET occurs between them, as noted above. Cleavage of the BoNT/B recognition and cleavage site results in the release of one or both of the fluorescent peptides into the cytosol, followed by degradation of the released peptide(s). As noted above, such released fluorescent peptides can include an amino acid or an amino acid sequence (e.g. a degron sequence) that enhances the rate of degradation following release into the cytosol relative to a corresponding peptide lacking such an amino acid or amino acid sequence. FIG. 3 shows an example of such a reporting construct pair.

In a preferred embodiment of the inventive concept a fluorescent peptide utilized in the construct is derived from green fluorescent protein (GFP) or a GFP mutation. It should be appreciated that in some embodiments one member of the fluorescent peptide pair can be retained on the vesicle membrane on exposure of a cell expressing the construct to BoNT/B. In embodiments where one of the fluorescent peptides is retained on the vesicle membrane following proteolysis by BoNT/B light chain, emission measurement from the retained fluorescent peptide can be used to normalize emission measurements made from the release fluorescent peptide. In embodiments where both fluorescent peptides are released from the vesicle membrane by the action of BoNT/B light chain proteolytic activity data normalization can be provided by the application of a reference dye (for example, a fluorescent cell membrane-binding dye with a distinguishable excitation and emission spectra).

Figure 4:
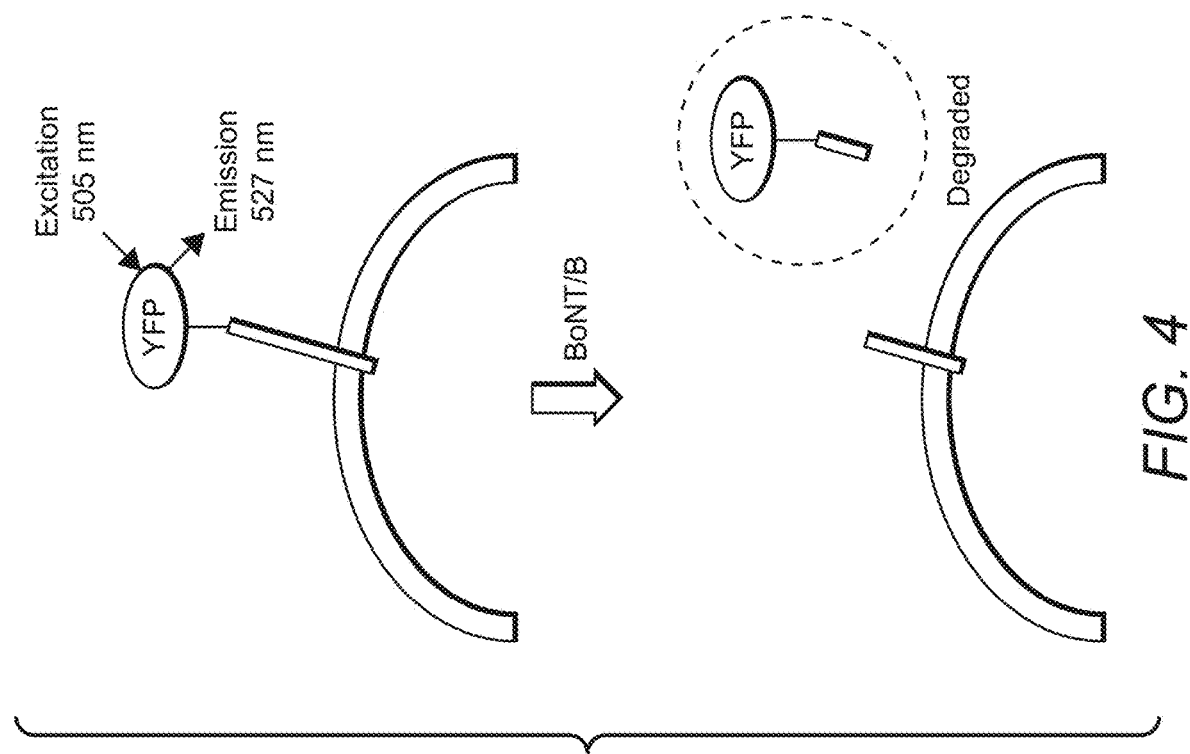
FIG. 4 shows an exemplary arrangement of the components of a reporting construct of the inventive concept.

In another embodiment of the inventive concept the reporting construct arranged as a single peptide that includes a synaptobrevin derived membrane binding region, a BoNT/B recognition and cleavage site, and a fluorescent peptide region. In a preferred embodiment the BoNT/B recognition and cleavage site is derived from synaptobrevin. Cleavage of the recognition and cleavage site results in release of the fluorescent peptide into the cytosol, where it can be subsequently degraded. In some embodiments the fluorescent peptide can include amino acid sequence modifications (such as incorporation of basic amino acids and/or a degron sequence) that enhance degradation on release into the cytosol relative to a corresponding peptide lacking such an amino acid or degron sequence. FIG. 4 shows an exemplary arrangement of the components of such a reporting construct.

In a preferred embodiment of the inventive concept a fluorescent peptide utilized in the construct is derived from green fluorescent protein (GFP) or a GFP mutation. In some embodiments data normalization can be provided by the application of a reference dye (for example, a fluorescent cell membrane-binding dye with a distinguishable excitation and emission spectra).

Figure 5:
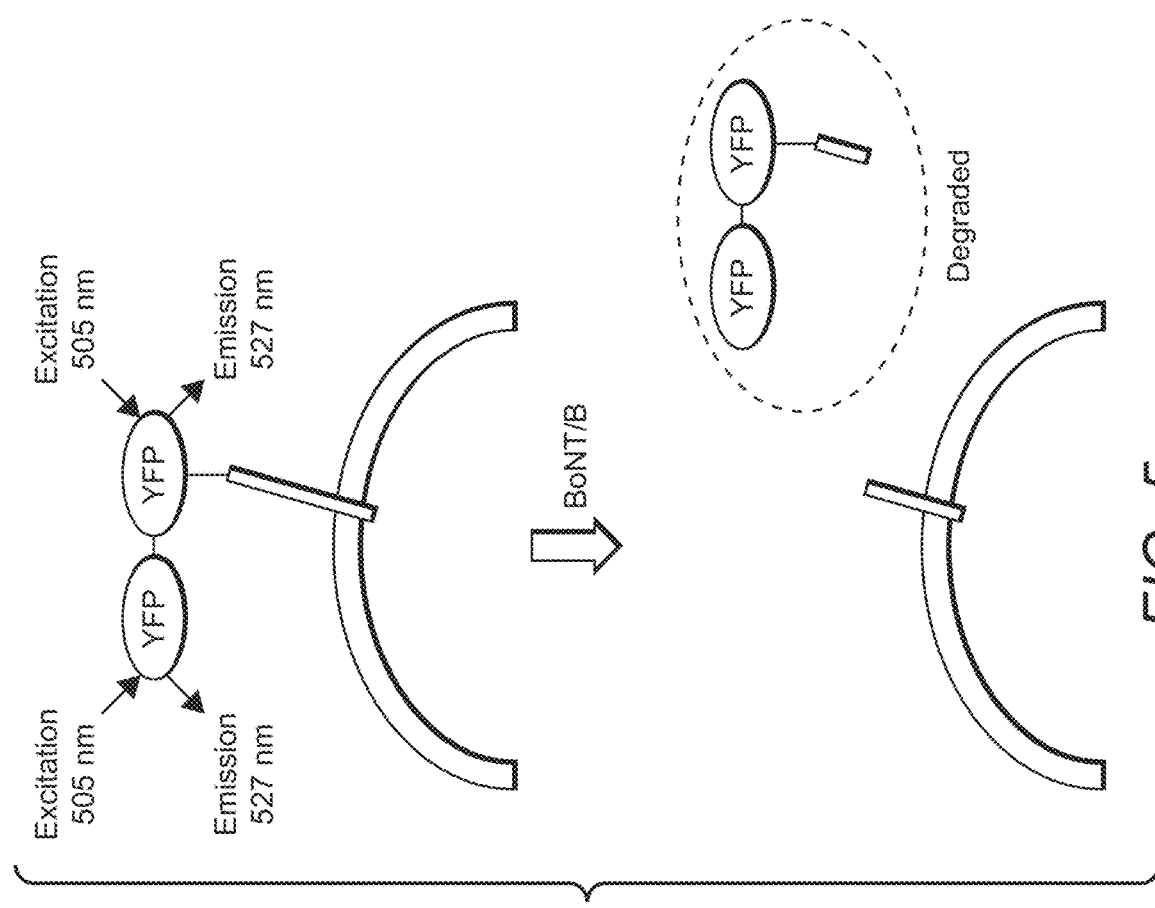
FIG. 5 shows another exemplary arrangement of the components of a reporting construct of the inventive concept.

In another embodiment of the inventive concept the reporting construct arranged as a single peptide that includes a synaptobrevin derived membrane binding region, a BoNT/B recognition and cleavage site, and a fluorescent peptide region that includes at least two identical fluorescing peptides linked to one another by a spacer peptide. Such a spacer peptide is purely structural and does not fluoresce, does not act as a BoNT/B substrate, and does not have a membrane binding function. In a preferred embodiment the BoNT/B recognition and cleavage site is derived from synaptobrevin. Cleavage of the recognition and cleavage site results in release of the fluorescent peptide region into the cytosol, where it can be subsequently degraded. As noted above, such a released fluorescent peptide can include an amino acid or amino acid sequence (e.g. a degron sequence) that enhances the rate of degradation relative to a corresponding peptide lacking such an amino acid or amino acid sequence. In some embodiments one or more of the fluorescent peptides can include amino acid sequence modifications (such as incorporation of basic amino acids) that enhance degradation on release into the cytosol. FIG. 5 shows an exemplary arrangement of the components of such a reporting construct.

Reporting constructs as described above can be expressed in cells that have been transformed and/or transduced (e.g. utilizing a virus), either transiently or permanently. As such, they can be encoded on one or more plasmids. In some embodiments such plasmids can be incorporated and/or integrated into the genome of a bacterial, fungal, or eukaryotic cell. In embodiments of the inventive concept that utilize two different peptides, both peptides can be encoded on a single plasmid. In other embodiments that utilize two different peptides, each peptide can be encoded on different plasmids. In such an embodiment the plasmids can include identical regulatory elements, or can include different regulatory elements that permit differential expression of the peptides.

Cells suitable for use in methods of the inventive concept include cells that are susceptible to BoNT/B intoxication. Such cells can include cell surface receptors for BoNT/B. Suitable cells can be presented as cells in cell culture (either primary or as cultured cell lines), and can be neuronal cells or derived from neuronal cells (for example, from tumors derived from neuronal cells). Alternatively suitable cells can include non-neuronally derived cells that have been modified, permanently or transiently, to express or otherwise possess suitable cell surface receptors. Suitable cells can be of human or animal (e.g. murine or rat) origin, and can include retinoblastoma cells, Neuro2A cells, M17 cells, PC12 cells, SK-N-SH cells, LNCaP cells, immortalized murine astrocytes (for example, SV40T cells), human and/or murine hTERT immortalized cells, iPSC neurons, stem cell derived neurons, and/or primary neurons.

As noted above, constructs of the inventive concept can be encoded on plasmids, which can in turn be used in the temporary and/or permanent transformation of cells. In instances where the reporting construct system includes a pair of reporter peptides, both can be encoded on a single plasmid. Alternatively, in some embodiments of the inventive concept the peptides of a reporting construct system that utilizes a pair of reporter peptides can be encoded on different plasmids. Examples of suitable peptides are shown in FIGS. 6A to H. A plasmid pMD0032 ORF (SEQ ID NO. 1) encodes for a YFP-synaptobrevin (VAMP2) peptide (FIG. 6A-A and FIG. 6A-B). A plasmid pMD0034 ORF encodes for another YFP-synaptobrevin (VAMP2) peptide (SEQ ID NO. 3; FIG. 6C-A and FIG. 6C-B) and another pMD0034 ORF encodes for a CFP-synaptobrevin (VAMP2) peptide (SEQ ID NO. 2; FIG. 6B-A and FIG. 6B-B). A plasmid pMD0071 ORF encodes for another YFP-synaptobrevin (VAMP2) peptide (SEQ ID NO. 5; FIG. 6E-A and FIG. 6E-B) and pMD0071 ORF encodes for CFP-synaptobrevin (VAMP2) (Q76V) peptide that includes an ECFP variant of CFP (SEQ ID NO. 4; FIG. 6D-A and FIG. 6D-B, which is not cleaved by BoNT/B). A plasmid pMD0183 ORF encodes for a YFP-YFP-synaptobrevin (VAMP2) peptide (SEQ ID NO. 8; FIG. 6F-A, FIG. 6F-B, FIG. 6F C, and FIG. 6F-D), which includes two YFP peptide sequences arranged in series. A plasmid pMD0185 ORF encodes for a CFP-synaptobrevin (VAMP2) peptide (SEQ ID NO. 6; FIG. 6G-A and FIG. 6G-B) and another pMD0185 ORF encodes for a YFP-synaptobrevin (VAMP2) (D64N, D68N, Q76V) peptide (SEQ ID NO. 7; FIG. 6H-A and FIG. 6H-B, which is not cleaved by BoNT/B).

Figure 7:
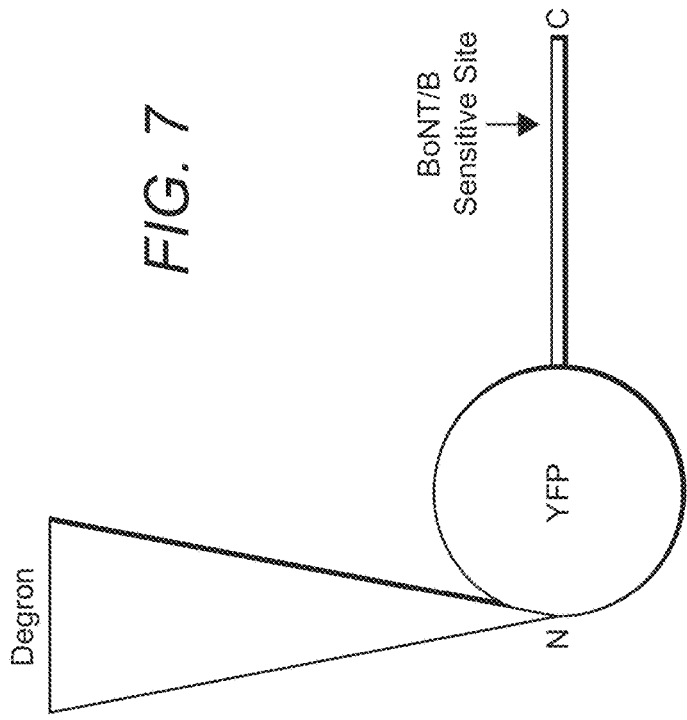
FIG. 7 depicts a typical reporting construct utilized in the characterization of a BoNT from a serotype B *Clostridium botulinum* (BoNT/B).

In some embodiments of the inventive concept, a reporting construct is provided that includes signaling components that generate a detectable signal, one or more degrons that increase the rate of intracellular digestion of associated peptide sequences, a protease cleavage site that is recognized and cleaved by a protease of interest (for example, a BoNT), and a localization sequence that localizes the intact reporting construct in a region within a cell that is relatively protected from intracellular digestion. Such components can be arranged in the following order: N-terminus:degron sequence:signaling sequence:protease substrate site:localization sequence. In some embodiments the localization sequence is part of the protease substrate site. In other embodiments the localization sequence is separate and distinct from the protease substrate site. A depiction of a typical reporting construct utilized in the characterization of a BoNT from a serotype B *Clostridium botulinum* (BoNT/B) is shown in FIG. 7. It should be appreciated that in such an embodiment the BoNT/B sensitive site can be synaptobrevin or a fragment of synaptobrevin that includes BoNT/B recognition and/or cleavage sites and a membrane localization region. While FIG. 7 depicts a construct for characterization of BoNT/B, Inventors contemplate that reporting constructs of the inventive concept can be used in cell-based or non-cell-based assays for any suitable protease and/or protease activity.

A variety of degron sequences can be utilized in reporting constructs of the inventive concept. For example, an N-terminal amino acid can be selected that increases the rate of intracellular degradation according to the N-end rule. In other embodiments of the inventive concept the degron can be selected from degron sequences of degron-containing peptide substrates, as shown in Table 1.

TABLE 1

| Degron Containing Peptides | Peptide Sequence |
|---|---|
| Bonger (SEQ ID NO. 11) | KTRGVEEVAEGVVLLRRRGNK |
| TAZ (SEQ ID NO. 12) | KPFLNGGPYHSREQSTDSGLGLGSYK |
| HIF-α (SEQ ID NO. 13) | ASADLDLEALAPYIPADDDFQLRK |
| iNOS (SEQ ID NO. 14) | KEEKDINNNVKKTK |
| SRC3 (SEQ ID NO. 15) | DVQKADVSSTGQGIDSK |
| Cyclin D1 (SEQ ID NO. 16) | KAAEEEESLASTPTDVRDVDIK |
| IFNAR1 (SEQ ID NO. 17) | KKYSSQTSQDSGNYSNK |
| p53 (SEQ ID NO. 18) | KPLSSSVPSQKTYQGSYGFRLGK |
| β-catenin (SEQ ID NO. 19) | KAWQQQSYLDSGIHSGATTTAPK |

Bold amino acids represent phosphorylated residues in phospho-degrons.

It should be appreciated that the localization sequence of the reporting construct can be selected to provide protection from intracellular degradation processes mediated by the N-end amino acid, for example by localizing the intact reporting construct at or near a cell membrane. Surprisingly, the inventors have found that the presence of a localizing sequence (e.g. the membrane-binding portion of synaptobrevin) can effectively prevent intracellular degradation of the intact reporting construct.

Reporting constructs of the inventive concept can utilize any suitable signaling sequence. Suitable signaling sequences include green fluorescent peptide, cyan fluorescent peptide, yellow fluorescent peptide, other green fluorescent peptide mutations, and other fluorescent peptides. In preferred embodiments two or more signaling sequences in a reporting construct are arranged such that no useful FRET (i.e. less than about 5% energy transfer) occurs between them. In other embodiments two or more fluorescent peptides can be arranged as a FRET pair within a signaling sequence. Other suitable signaling sequences include luciferase, aequorin, and other light emitting sequences. As noted above, in some embodiments of the inventive concept a second signaling sequence can be associated with or coupled to the localization sequence of the reporting construct, such that the second signaling sequence remains within the protected region of the cell following cleavage of the reporting construct. In such embodiments the second signaling sequence can be used for normalization of the signal provided by the released signaling sequence, cell numbers between different test sites or wells, and distribution of cells within a test site or well.

Signaling sequences can directly adjoin a degron sequence located at or near the N-terminus of the reporting construct. Alternatively, a signaling sequence can be separated from the degron sequence by a spacer or linker region. Such a spacer or linker can be rigid, flexible, or include both rigid and flexible regions. Such a spacer can advantageously improve the access of components of intracellular protein degradation systems by relieving steric hindrance.

Reporting constructs of the inventive concept can utilize a wide variety of intracellular protease substrate sites. Suitable intracellular protease substrate sites include caspase sensitive sites, tetanus toxin sensitive sites, BoNT sensitive sites (i.e. sites that are susceptible to cleavage by BoNT/A, BoNT/B, BoNT/C, BoNT/D, BoNT/E, BoNT/F, and/or BoNT/G), and anthrax toxin sensitive sites. In some embodiments, the protease substrate site can include both protease recognition sites (i.e. sites to which the protease has an affinity) and protease cleavage sites (i.e. the specific site at which the peptide chain is cleaved). Such protease recognition sites and protease cleavage sites can be a continuous or a discontinuous sequence. In some embodiments, for example a BoNT/B sensitive reporting construct, the protease substrate site can include a localization sequence that maintains the intact reporting construct at a protected location within the cell.

Reporting constructs of the inventive concept can utilize a wide variety of localization sequences that can localize the intact reporting construct at location within the cell that is protected or partially protected from intracellular protein degradative process that are mediated by the degron sequence. Such protected sites include cell membranes, such as the interior of the plasma membrane, rough ER membrane, smooth ER membrane, vesicle membranes, and nuclear membranes. For example, a localization sequence provided by a BoNT/B protease substrate sequence can localize the intact reporting construct to a vesicle surface where it is protected or partially protected from intracellular degradative processes. In some embodiments the localization sequence can be provided as part of a protease substrate sequence. In other embodiments the localization sequence can be a distinct and separate peptide sequence that is not directly related to the protease substrate sequence. In some embodiments a localization sequence from one intracellular protease substrate sequence (for example, a BoNT/A substrate sequence) can be utilized in a reporting construct having an unrelated second intracellular protease substrate sequence (for example, a BoNT/B substrate sequence, a caspase substrate sequence, or an anthrax toxin substrate sequence).

As noted, the above described reporting constructs can be utilized in cell-based assays. In such embodiments the reporting construct can be encoded on one or more plasmids utilized to transform, either permanently or transiently, cells utilized in such assays. In a preferred embodiment such a transformed cell would express one or more types of surface receptor that provides specific uptake of an analyte in culture media. Such an analyte could trigger production of the intracellular protease to be characterized or, alternatively can include the intracellular protease to be analyzed (for example, BoNTs). Such cells can be tumor derived or otherwise immortalized to provide cell lines suitable for use in cell-based assays. Alternatively, reporting constructs can be introduced into cells that do not encode for them by physical and/or chemical means, such as ultrasound, electroporation, or fusion with encapsulating vesicles. In a preferred embodiment the cells are neuronally-derived cells that include receptors for a specified BoNT neurotoxin, and that have been transformed to express a reporting construct that includes a corresponding BoNT substrate site.

Another embodiment of the inventive concept is a cell-based assay for protease activity. Such protease activity can be a result of the activity of an analyte after it is internalized by a cell, or can be associated with a protease that is produced by the cell in response to the presence of an analyte or another environmental condition. In such a cell-based assay one or more cells that include a reporting construct of the inventive concept are provided. Such cells are exposed to a culture medium, sample, and/or environmental condition that includes the analyte to be characterized. The cells can be observed for signal originating from the reporting construct prior to or immediately following exposure to the analyte in order to obtain a baseline signal. Following exposure to the analyte the cell or cells are monitored and additional signal data from the reporting construct obtained. Such monitoring can be continuous, intermittent, or include only a single observation that follows a defined time period. Comparison of the post-exposure to signal to the baseline signal can be used to characterize amount, activity, and/or other properties of the analyte. For example, exposure of a series of test sites containing suitable cells and exposed to a series of samples containing known concentrations of the analyte of interest can be used to derive a dose/response curve, which can subsequently be used to estimate concentration of the analyte in an unknown sample. Such assays can have particular utility in replacing animal studies of toxicity or pharmaceutical effect.

In another embodiment of the inventive concept, a population of cells susceptible to BoNT/B intoxication is genetically altered, either temporarily or permanently, to express at least one of the above described reporter constructs. Images are obtained of a field containing one or more of such cells at wavelengths corresponding to an emission wavelength of at least one of the fluorescent peptides that can be released by BoNT/B proteolytic activity, prior to the exposure of such transformed cells to BoNT/B. It should be appreciated that such cells are not generally positioned in a predetermined or ordered fashion, and can be distributed randomly or essentially randomly within the field. Such imaging takes place while illuminating the field at the excitation wavelength of the fluorescent peptide and recording the image at the emission wavelength of the fluorescing peptide. In embodiments where a fluorescent peptide is present that is not released by BoNT/B activity an additional image can be obtained while illuminating the field at the corresponding excitation wavelength and recording the image at the corresponding emission wavelength of this fluorescent peptide. Following the application of sample containing (or thought to contain) BoNT/B to the cells the same field is re-imaged at least once after a suitable time interval. Image recognition software is then applied to the image recorded prior to BoNT/B application to identify regions of the image that do show useful fluorescence (e.g. cell-free regions, cells that do not express a reporting construct) and to identify regions that exceed a pre-defined signal threshold (for example, a value representing CCD saturation and/or nonlinearity). Upon exclusion of such portions of the image the remaining regions represent a quantitation mask. This quantitation mask is applied to subsequent images obtained following exposure of the field to BoNT/B. In this fashion data is selectively obtained only from cells expressing the reporting construct at the desired level or within a desired range. Such selective collection of data from relevant portions of the test area can reduce interference from scatter and background fluorescence, and advantageously reduce variation and/or improve sensitivity.

A self-correcting intensity value can be obtained from images processed in this fashion by combining pixel intensity values with the total area included within the quantitation mask. For example, average pixel intensity throughout the quantitation mask can be multiplied by the area of the quantitation mask to derive a fluorescence intensity for that image. Fluorescence intensity values obtained from a given field after exposure to BoNT/B can be compared to fluorescence intensity values obtained prior to exposure to BoNT/B, and the result used to accurately estimate the effect of BoNT/B on the distribution and/or degradation of a fluorescent peptide released from the reporting construct by BoNT/B activity. Such values can be further normalized through the use of similar measurements obtained from fluorescent peptides that are not released by BoNT/B activity. Such an embodiment can be used in methods for quantifying or otherwise characterizing BoNT/B activity, for example by comparing results obtained from an unknown sample to results obtained from a set of samples containing known amounts of BoNT/B.

Alternatively, such a method can be used to identify cell lines and/or constructs that are suitably responsive to BoNT/B, with subsequent characterization of BoNT/B being carried out by methods that use such cell lines and/or constructs and acquire data using a conventional, non-imaging fluorometer. It should be appreciated that such a characterization method is generally applicable to cell-based assays and other assays where results are variable and localized to specific areas (which may or may not be randomly positioned within an observed field) within an image, and is not restricted to use with cells and/or BoNT/B. It should also be appreciated that such a characterization method can be effectively applied when only a portion of the potential test sites (for example, cells) are functional within the proscribed test parameters. For example, a characterization method of the inventive concept can be applied to a field containing transformed cells that express a reporting construct, where less than 90%, less than 80%, less than 70%, less than 60%, less than 50%, less than 40%, less than 30%, less than 20%, or less than 10% of the cells in the field express the reporting construct at levels that are suitable for use in an assay.

In some embodiments of the inventive concept, a quantitation mask-based imaging method as described above can be used as a primary assay. In other embodiments of the inventive concept such a quantitation-mask based imaging method can be used to identify populations of cells, cell types, reporting construct configurations, or combination thereof that produce an acceptable result. Once identified such optimized cell-based reagents can be used as the basis of a non-imaging method where fluorescence data is gathered using a conventional (e.g. microwell plate) fluorometer that does not have imaging capability, but rather quantifies total fluorescence of a testing region.

EXAMPLES

Figure 8A:
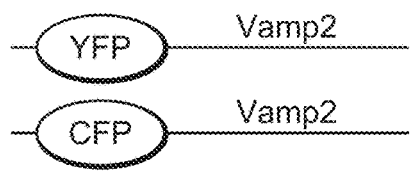
FIGS. 8A and 8B schematically depict reporting construct pairs of the inventive concept.
Figure 8B:
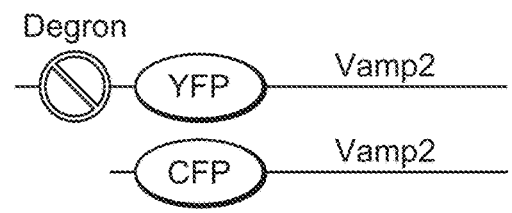

A series of reporting peptide construct pairs were prepared, where each reporting peptide construct included a synaptobrevin (Vamp2) portion coupled to the carboxyl terminus of either a YFP peptide or a CFP peptide. This arrangement is shown schematically in FIG. 8A. Variations on this basic architecture inserted a degron sequence into a peptide sequence coupled to the N terminus of the YFP peptide (see FIG. 8B) to generate a series of degron-containing reporting constructs. Designations and degron content of the YFP-bearing constructs are shown in Table 2. The YFP constructs were paired with a common CFP-bearing construct (SEQ ID NO. 21) that did not include a degron sequence to provide the reporting peptide construct pairs. In this example the CFP-bearing construct (SEQ ID NO. 21) includes point mutations that prevent cleavage by BoNT/B (e.g. D64N, D65N, D68N, Q76V) while preserving the majority of the VAMP2 sequence and structure. As a result the CFP portion of the CFP-bearing construct remains localized in transformed cells and is not degraded at an accelerated rate following exposure to BoNT/B activity.

TABLE 2

| Degron Sequence | Designation |
|---|---|
| None (Control) | pMD0185 (SEQ ID NO. 20) |
| Bonger | pMD0189 (SEQ ID NO. 11; SEQ ID NO. 22) |
| iNOS | pMD0190 (SEQ ID NO. 23) |
| p53 | pMD0191 (SEQ ID NO. 9) |
| SNAP-25 | pMD0192 (SEQ ID NO. 10) |

Neuro2A (neuroblastoma) cells were seeded in EMEM+ 10% FBS at $2.0 \times 10^4$ cells per well in 96 well poly D-lysine coated tissue culture plates. The cells were allowed to recover for 18 (±2) hours. Cells were then washed with 100 µL serum-free EMEM following by a 30 minute incubation in serum-free EMEM (100 µL per well). Transfection reagents were prepared by preparing two 1.5 mL Eppendorf tubes as follows: Tube A—0.5 mL serum-free EMEM and 2.8 mg of plasmid DNA; Tube B—0.5 mL serum-free EMEM and 7.0 µL of lipofectamine 2000™ (Life Technologies). Tubes A and B were incubated at room temperature for 5 minutes, then mixed with one another incubated for an additional 20 minutes. 25 µL of this transfection mixture was added to a well containing cells in order to provide a transient transfection.

Cells were incubated with the transfecting DNA for 18 hours, then treated with BoNT/B for 48 hours. Cells were imaged using a GE InCell™ automated cell imager at 10× objective using brightfield, YFP, and CFP filter sets. Following this imaging the plates were washed with PBS in an automated plate washer and fluorophore emission intensities characterized using a Tecan F500™ plate reader.

Figure 9A:
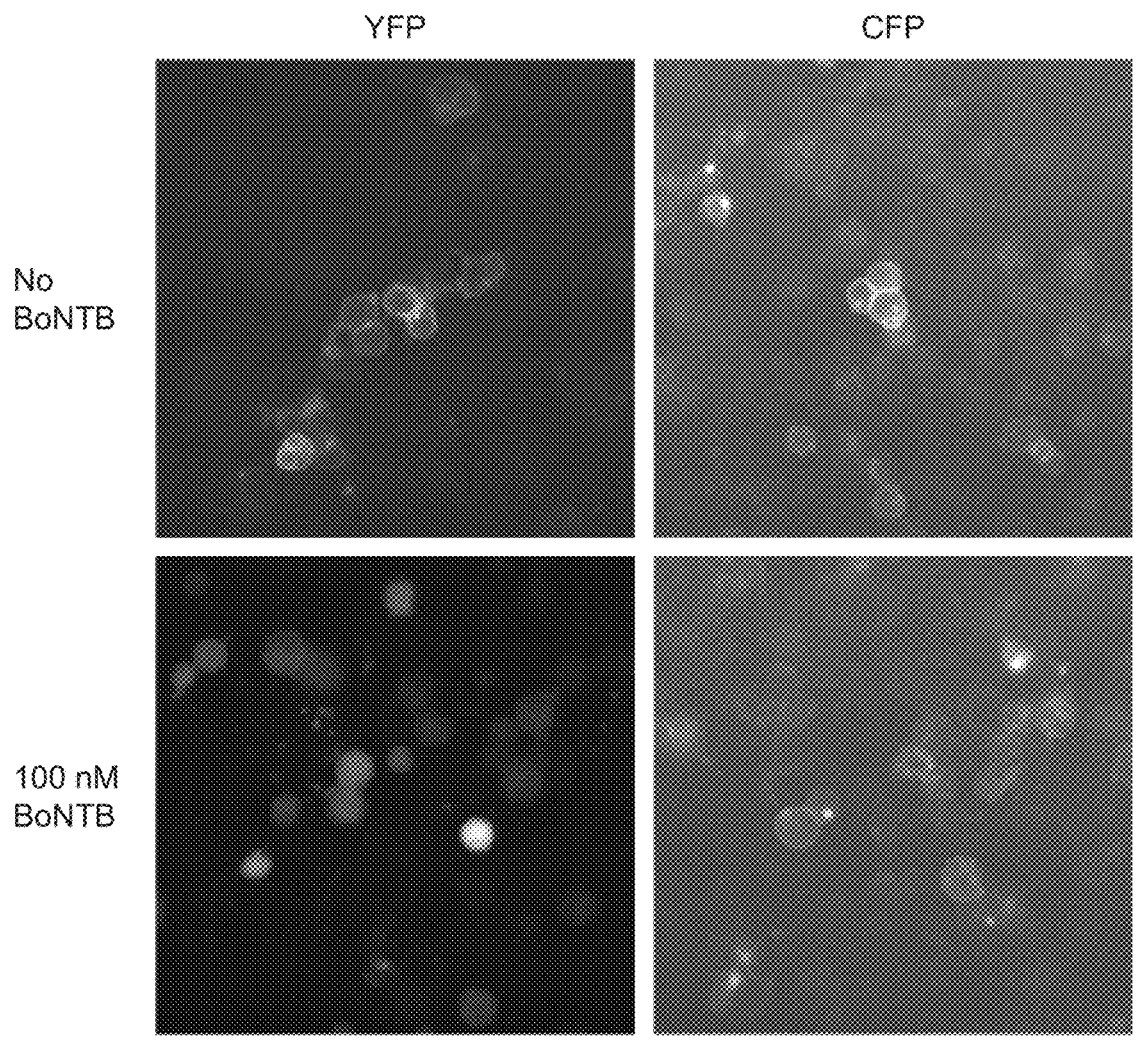
FIGS. 9A and 9B show the results of exposure of transformed cells carrying reporting construct pairs of the inventive concept to BoNT/B.
Figure 9B:
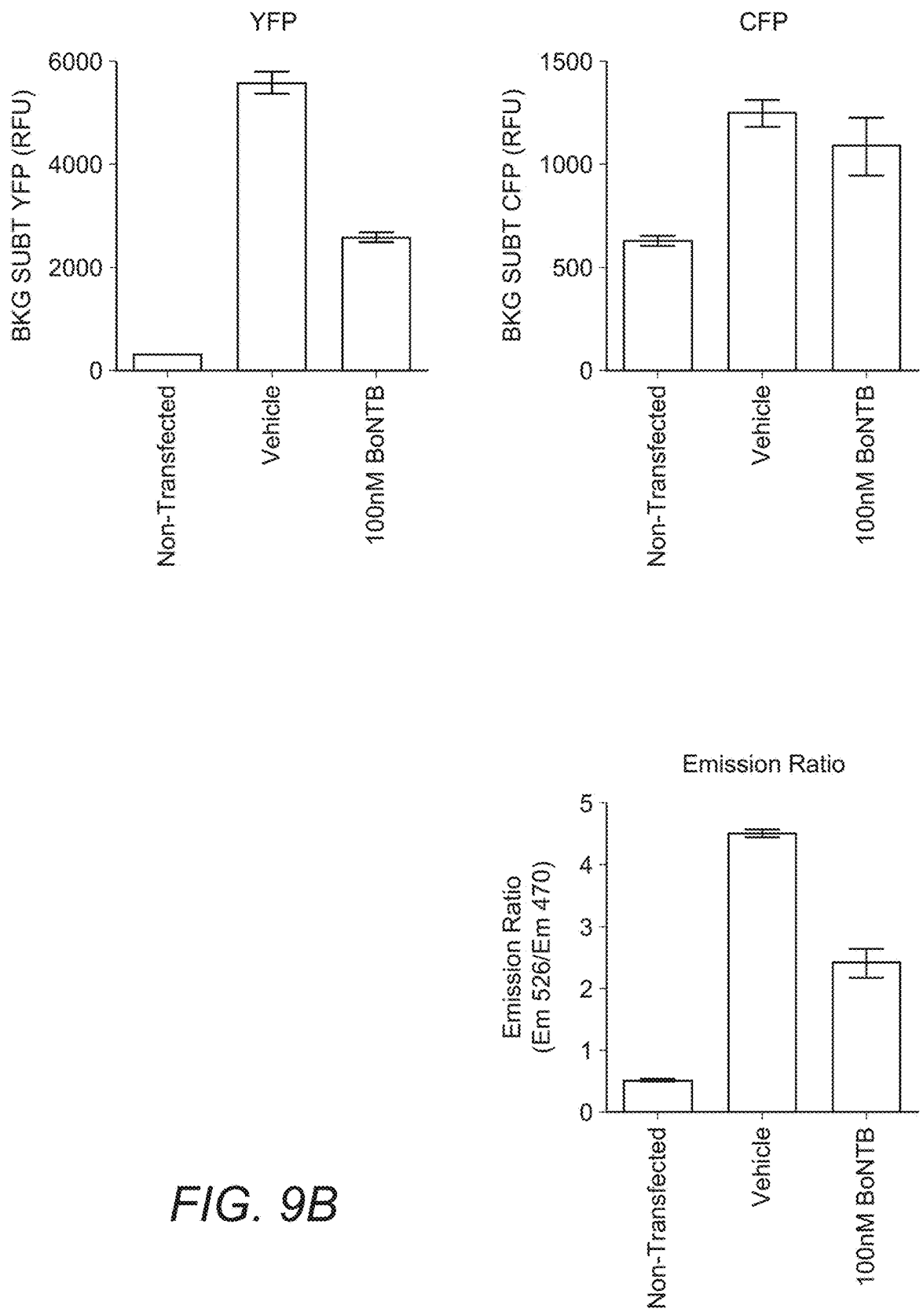

FIG. 9A shows a photomicrograph of cells expressing the control (i.e. no degron sequence) reporting construct in the presence and absence of BoNT/B. Emissions from YFP and CFP fluorescent peptides are shown. In the absence of BoNT/B, YFP emission is localized in vesicles. In the presence of BoNT/B YFP emissions are re-localized, with diffusion of a YFP-containing peptide apparent throughout the cell. Localization of the CFP containing construct does not change due to the presence of point mutations that prevent cleavage by BoNT/B activity. FIG. 9B shows overall fluorescence emission from such cells as characterized using a fluorescence plate reader. Non-transfected cells were also characterized. As shown, YFP emission is sharply reduced in transformed cells exposed to BoNT/B, whereas CFP emission is relatively unaffected (the means of individual measurements at different BoNT/B concentrations falling within the variation of those measurements). As a result the results of YFP emission to CFP emission ratios parallel those of YFP emission.

Figure 10A:
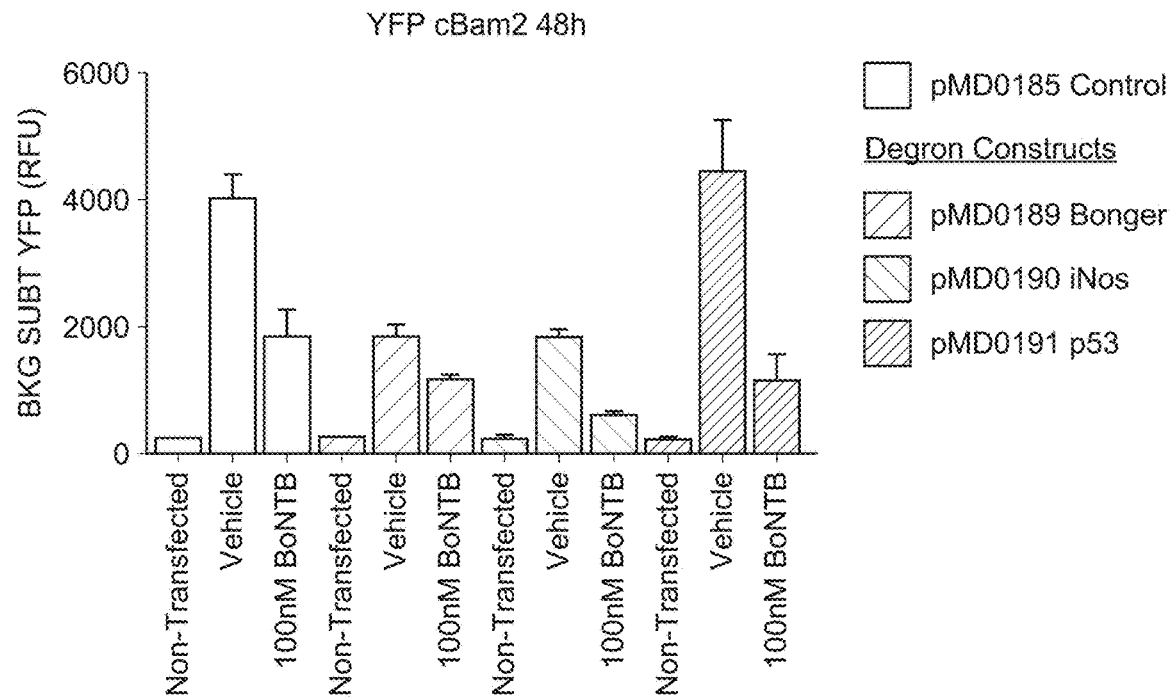
FIGS. 10A to 10C show the results of fluorescence measurements made from non-transformed cells, cells transformed to express a control (i.e. not containing degron) reporting construct pair, and cells transformed to express reporting construct pairs in which the YFP-bearing construct included a degron sequence positioned towards the N-terminus relative to the YFP peptide.
Figure 10B:
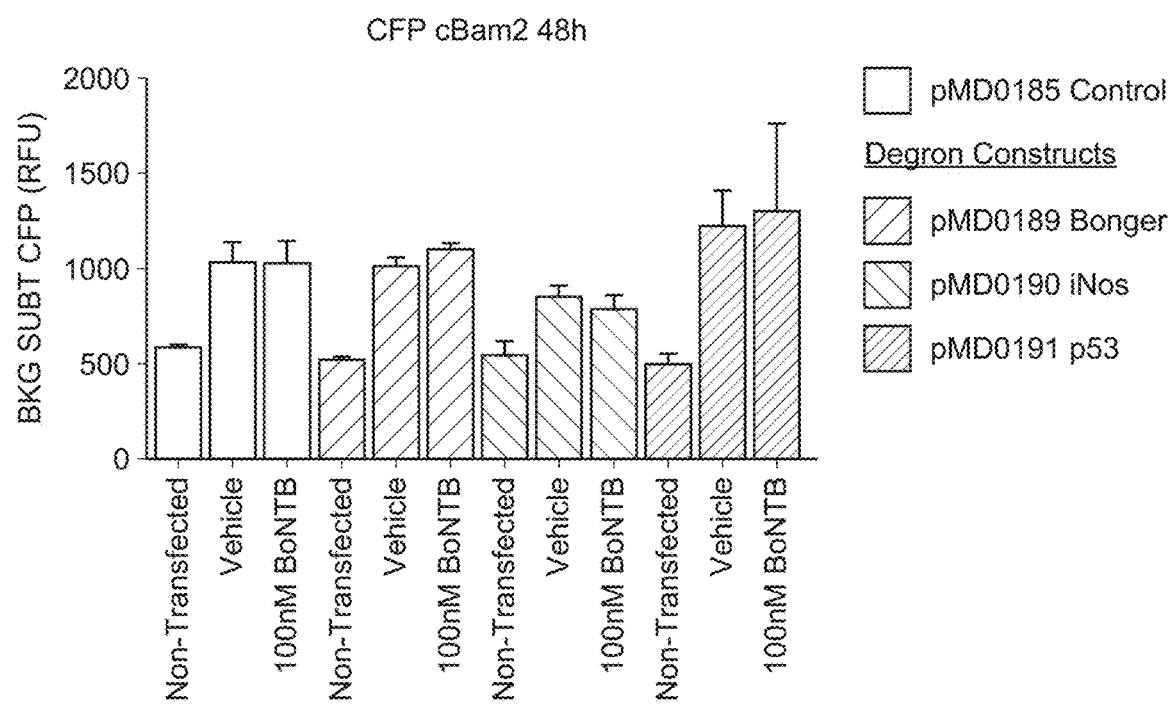
Figure 10C:
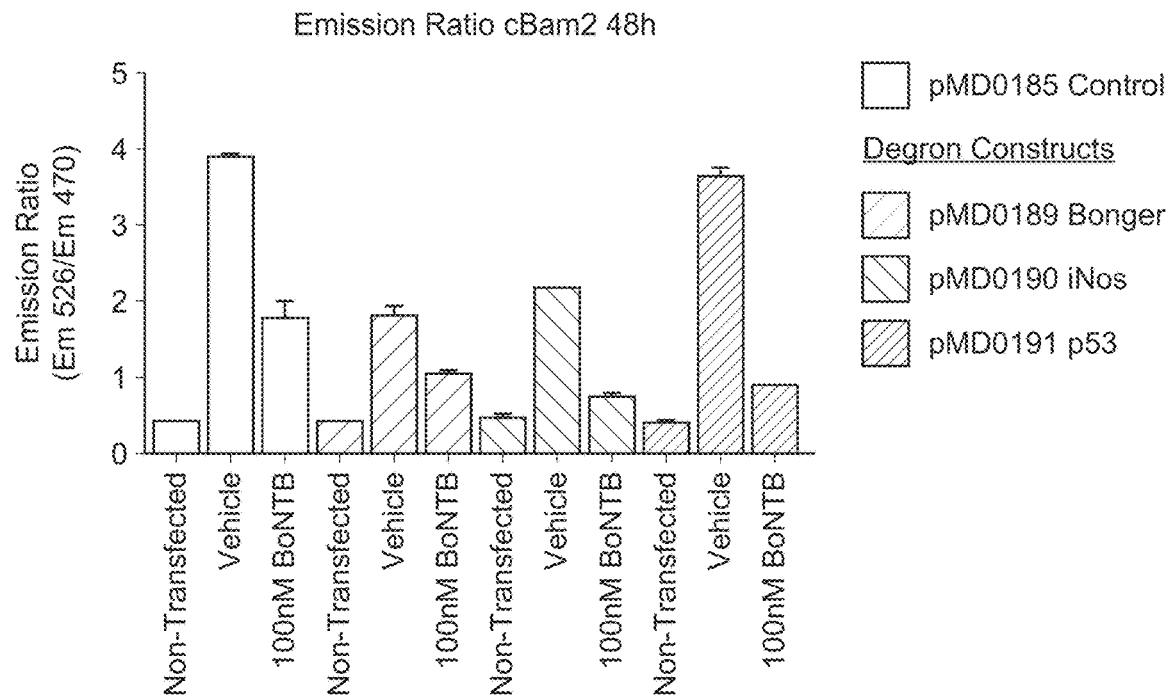

FIGS. 10A to 10C show the results of fluorescence measurements made from non-transformed cells, cells transformed to express a control (i.e. not containing degron) reporting construct pair, and cells transformed to express reporting construct pairs in which the YFP-bearing construct included a degron sequence positioned towards the N-terminus relative to the YFP peptide. FIG. 10A shows the results of measurements of YFP emission in the presence and absence of BoNT/B. FIG. 10B shows the results of measurements of CFP emission in the presence and absence of BoNT/B. FIG. 10C shows the results of measurements of YFP fluorescence:CFP fluorescence ratio in the presence and absence of BoNT/B. Results are summarized below in Table 3. It is apparent that inclusion of degron sequences (e.g. iNOS and/or p53 degron sequences) positioned N-terminally from the YFP portion of the YFP-bearing member of the reporting construct pair can provide improved dynamic range in a BoNT/B cell-based assay, relative to cells transformed using an analogous construct pair lacking the degron sequence.

TABLE 3

| Construct | Vehicle Only (YFP:CFP ratio) | 100 nM BoNT/B (YFP:CFP ratio) | Dynamic Range |
|---|---|---|---|
| pMD0185 (no degron) | 3.90 | 1.78 | 2.20 |
| pMD0189 (Bonger) | 1.82 | 1.04 | 1.75 |
| pMD0190 (iNOS) | 2.17 | 0.74 | 2.93 |
| pMD0191 (p53) | 3.63 | 0.89 | 4.09 |

Dynamic Range = (YFP:CFP emission ratio with vehicle-only) ÷ (YFP:CFP emission ratio with vehicle + 100 nm BoNT/B)

Figure 11A:
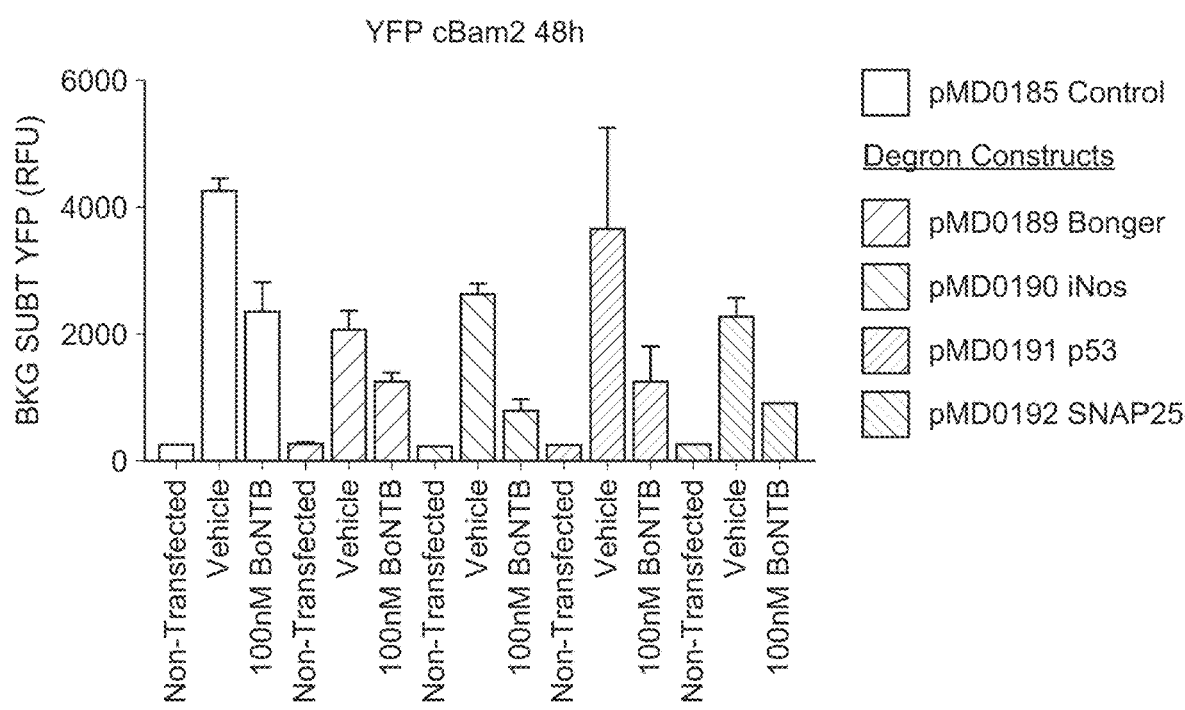
FIGS. 11A to 11C shows results of studies similar to those of FIG. 10A to 10C, incorporating an additional cell population transformed to express a reporting construct pair with a degron sequence obtained from SNAP-25.
Figure 11B:
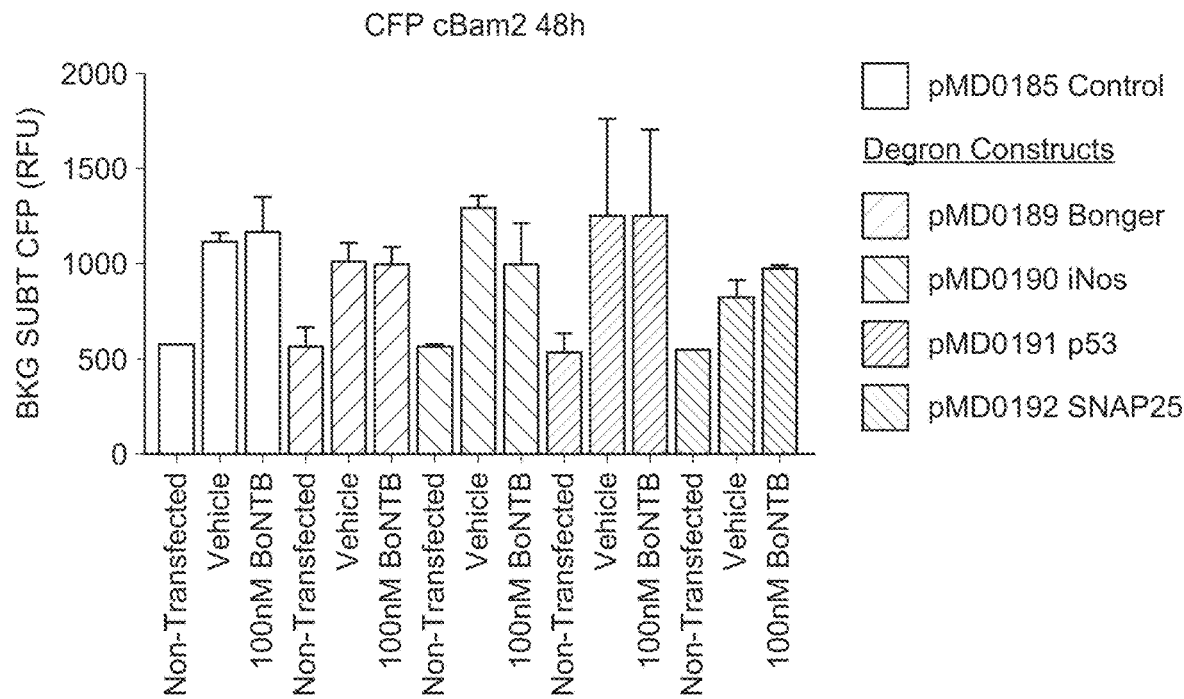
Figure 11C:
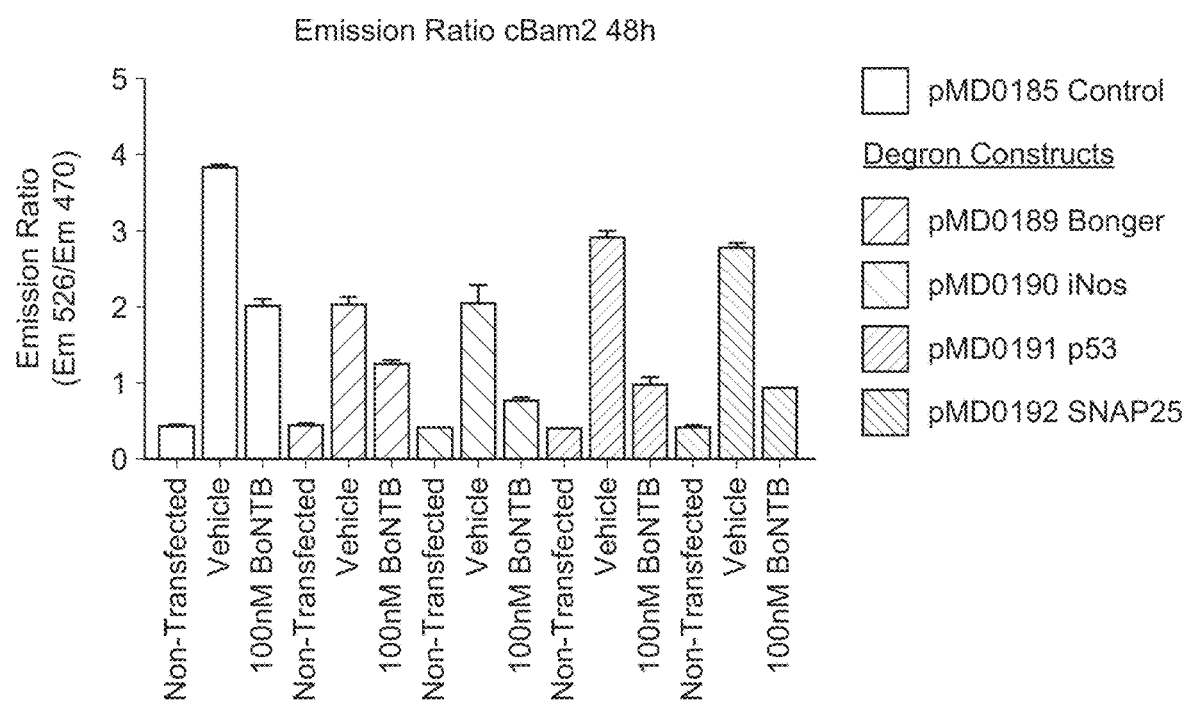

FIGS. 11A to 11C show the results of similar studies performed using an additional set of cells transformed using a reporting construct pair that incorporates a degron sequence from SNAP-25 positioned towards the N-terminus relative to the YFP peptide. FIG. 11A shows the results of measurements of YFP emission in the presence and absence of BoNT/B. FIG. 11B shows the results of measurements of CFP emission in the presence and absence of BoNT/B. FIG. 11C shows the results of measurements of YFP fluorescence:CFP fluorescence ratio in the presence and absence of BoNT/B. Results are summarized below in Table 4. It is apparent that inclusion of degron sequences (e.g. iNOS, p53, and/or SNAP-25 degron sequences) positioned N-terminally from the YFP portion of the YFP-bearing member of the reporting construct pair can provide improved dynamic range in a BoNT/B cell-based assay, relative to cells transformed using an analogous construct pair lacking the degron sequence.

TABLE 4

| Construct | Vehicle Only (YFP:CFP ratio) | 100 nM BoNT/B (YFP:CFP ratio) | Dynamic Range |
|---|---|---|---|
| pMD0185 (no degron) | 3.80 | 1.99 | 1.91 |
| pMD0189 (Bonger) | 2.02 | 1.23 | 1.64 |
| pMD0190 (iNOS) | 2.04 | 0.76 | 2.70 |
| pMD0191 (p53) | 2.90 | 0.96 | 3.01 |
| pMD0192 (SNAP-25) | 2.77 | 0.91 | 3.03 |

Dynamic Range = (YFP:CFP emission ratio with vehicle-only) ÷ (YFP:CFP emission ratio with vehicle + 100 nm BoNT/B)

Figures 12A, 12B:
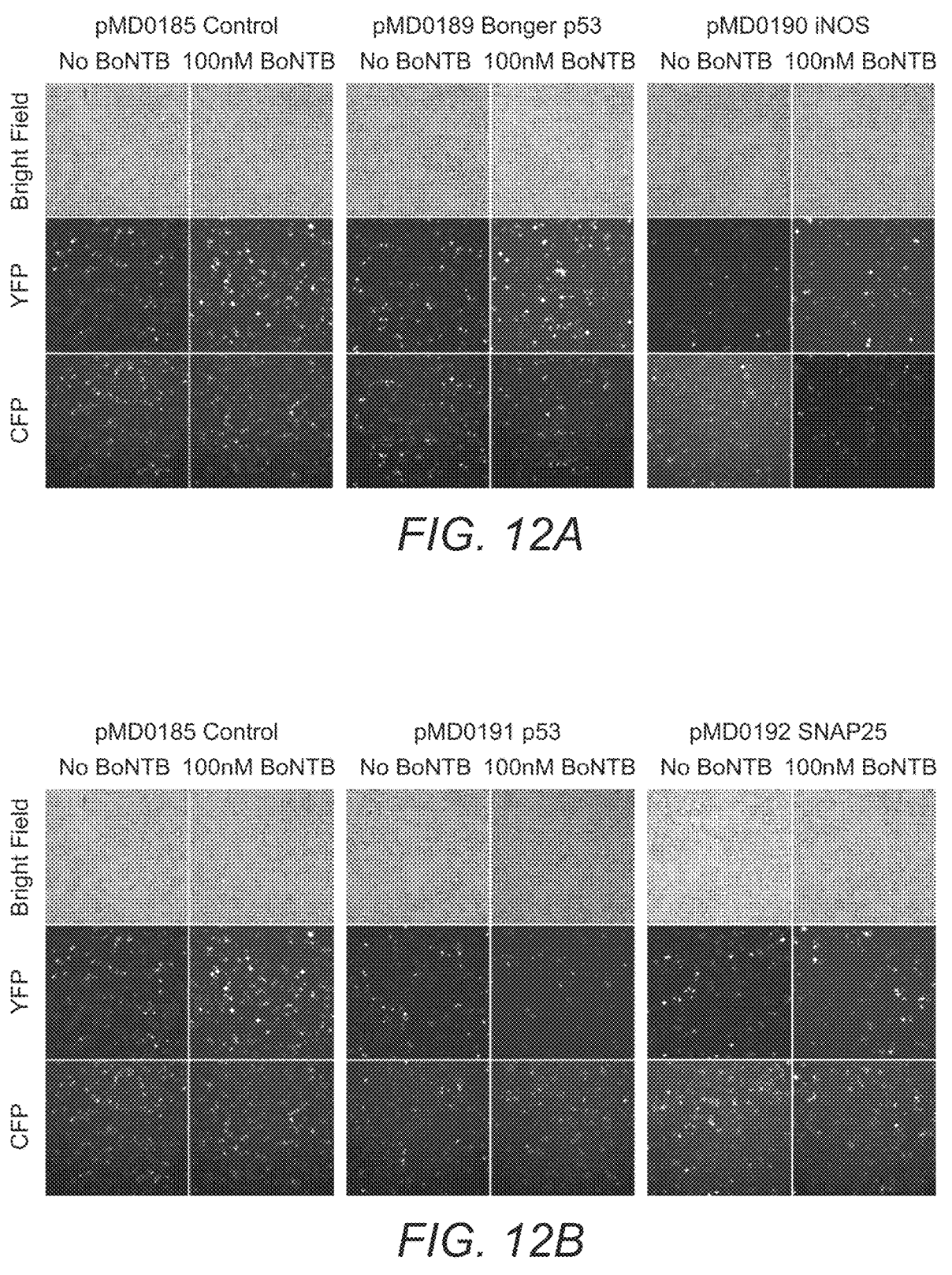

Surprisingly, Inventors have found that inclusion of a degron sequence position N-terminally to a fluorescent peptide portion of a reporting construct can modify cytosolic relocalization of the fluorescent peptide on release from the reporting construct (for example, by proteolytic activity of a botulinum neurotoxin). This is evident in the photomicrographs shown in FIGS. 12A and 12B. FIG. 12A shows brightfield, YFP emission, and CFP emission from transformed cells expressing a control reporting construct pair (containing no degron sequence) and transformed cells expressing reporting construct pairs that include degron sequences (specifically, Bonger or iNOS degron sequences) positioned N-terminally to the YFP peptide of the YFP-bearing member of the reporting construct pair. Images were taken in the presence and in the absence of BoNT/B. The cells carrying the pMD0190 constructs (which showed improved dynamic range relative to control cells on exposure to BoNT/B) showed reduced YFP fluorescence and less cytosolic relocalization of YFP-bearing peptide than control cells following exposure to BoNT/B. FIG. 12B shows the results of similar studies performed using cells carrying either the pMD0191 or pMD0192 reporting construct pairs, both of which show improved dynamic range on exposure to BoNT/B relative to control cells. The cells carrying the pMD0191 and pMD0192 constructs also showed reduced YFP fluorescence and less cytosolic relocalization of YFP-bearing peptide than control cells following exposure to BoNT/B.

Figure 13:
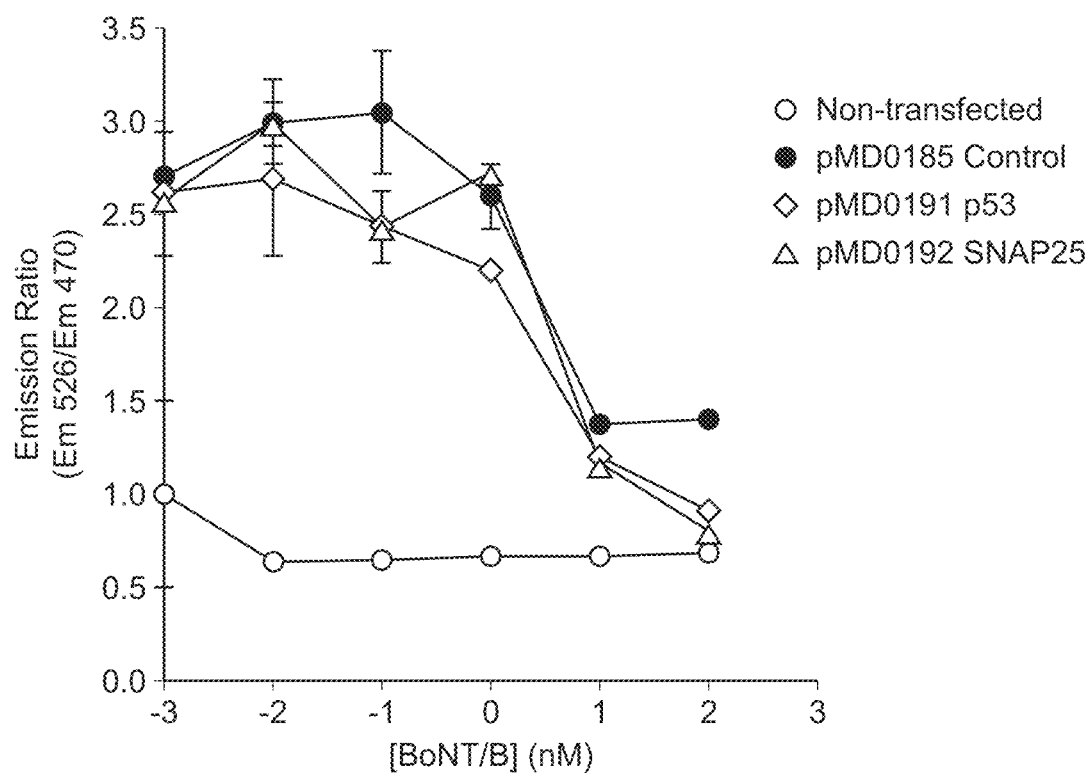
FIG. 13 shows results of application of BoNT/B at different concentrations to cells expressing a control BoNT/B-reactive construct pair lacking a degron sequence and cells expressing analogous BoNT/B-reactive construct pair where the YFP-bearing peptide includes a degron sequence.

Results of application of BoNT/B at different concentrations to cells expressing a control BoNT/B-reactive construct pair lacking a degron sequence and cells expressing analogous BoNT/B-reactive construct pair where the YFP-bearing peptide includes a degron sequence are shown in FIG. 13. In such assays increasing BoNT/B concentrations are associated with a decreasing YFP emission, which results in a decreasing YFP emission:CFP emission ratio. As shown, cells expressing the control construct pair (pMD0185) reach maximum emission ratio (indicating assay saturation) at approximately 1 nM BoNT/B. Cells expressing a p53 degron-containing construct, however, do not reach assay saturation until approximately $10^{-2}$ nM BoNT/B, indicating a substantial improvement in sensitivity.

In some embodiments, methods described above can be performed manually. In other embodiments, certain aspects of a method (for example, sample and/or reagent dispensing, transportation of labware in and out of an incubator, etc.) can be performed in an automated fashion, while other aspects can be performed manually. In other embodiments a method of the inventive concept essentially all of the steps of the method can be performed in an automated fashion, for example through the use of a programmable laboratory robot.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A reporting peptide construct pair for detection of a protease activity, comprising:
   a first peptide comprising:
      an N-terminal region and a first C-terminus, wherein the N-terminal region is a degron selected from the group consisting of SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, and SEQ ID NO. 19;
      a first localization sequence positioned at or near the first C-terminus, wherein the first localization sequence is configured to localize the first peptide in a protected site wherein the first peptide is protected from an intracellular protein degradation system that interacts with the degron;
      a first signaling sequence interposed between the degron and the first localization sequence; and
      a protease substrate sequence interposed between the first signaling sequence and the first localization sequence, such that the first signaling sequence is interposed between the degron and the protease substrate sequence; and
   a second peptide comprising:
      an N-terminus and a second C-terminus;
      a second localization sequence positioned at or near the second C-terminus, wherein the second localization sequence is selected to localize the second peptide in the protected region;
      a second signaling sequence; and
      a protease substrate analog sequence interposed between the second signaling sequence and the second localization sequence, wherein the protease substrate analog sequence is selected to show a reduced rate of cleavage relative to the protease substrate sequence when exposed to the protease activity,
   wherein the protease activity is botulinum neurotoxin protease activity and the protease substrate sequence is a substrate for the botulinum neurotoxin.

2. The reporting peptide construct pair of claim 1, wherein the protected site comprises a plasma membrane, a rough ER membrane, a smooth ER membrane, a vesicle membrane, and a nuclear membrane.

3. The reporting peptide construct pair of claim 1, wherein the first signaling sequence or the second signaling sequence comprises a fluorescent peptide sequence.

4. The reporting peptide construct pair of claim 1, wherein the protease substrate sequence comprises a botulinum neurotoxin (BoNT) substrate sequence selected from the group consisting of a BoNT/A substrate sequence, a BoNT/B substrate sequence, a BoNT/C substrate sequence, a BoNT/D substrate sequence, a BoNT/E substrate sequence, a BoNT/F substrate sequence, and a BoNT/G substrate sequence.

5. A cell comprising a reporting peptide construct pair for detection of a protease activity, wherein the reporting peptide construct pair comprises:

a first peptide comprising:
  an N-terminal region and a first C-terminus, wherein the N-terminal region is a degron selected from the group consisting of SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, and SEQ ID NO. 19;
  a first localization sequence positioned at or near the first C-terminus, wherein the first localization sequence is configured to localize the first peptide in a protected site wherein the first peptide is protected from an intracellular protein degradation system that interacts with the degron;
  a first signaling sequence positioned proximal to the degron; and
  a protease substrate sequence interposed between the first signaling sequence and the first localization sequence, such that the first signaling sequence is interposed between the degron and the protease substrate sequence; and
a second peptide comprising:
  an N-terminus and a second C-terminus;
  a second localization sequence positioned at or near the second C-terminus, wherein the second localization sequence is selected to localize the second peptide in the protected region;
  a second signaling sequence; and
  a protease substrate analog sequence interposed between the second signaling sequence and the second localization sequence, wherein the protease substrate analog sequence is selected to show a reduced rate of cleavage relative to the protease substrate sequence when exposed to the protease activity,
  wherein the protease activity is botulinum neurotoxin protease activity and the protease substrate sequence is a substrate for the botulinum neurotoxin.

6. The cell of claim 5, wherein the protected site comprises a plasma membrane, a rough ER membrane, a smooth ER membrane, a vesicle membrane, and a nuclear membrane.

7. The cell of claim 5, wherein the first signaling sequence or the second signaling sequence comprises a fluorescent peptide sequence.

8. The cell of claim 5, wherein the protease substrate sequence comprises a botulinum neurotoxin (BoNT) substrate sequence selected from the group consisting of a BoNT/A substrate sequence, a BoNT/B substrate sequence, a BoNT/C substrate sequence, a BoNT/D substrate sequence, a BoNT/E substrate sequence, a BoNT/F substrate sequence, and a BoNT/G substrate sequence.

9. The cell of claim 5, wherein the cell is a neuron or neuronally-derived cell.

* * * * *